US012623008B2

(12) United States Patent
Suffritti et al.

(10) Patent No.: US 12,623,008 B2
(45) Date of Patent: May 12, 2026

(54) APPARATUS FOR EXTRACORPOREAL BLOOD TREATMENT

(71) Applicant: GAMBRO LUNDIA AB, Lund (SE)

(72) Inventors: Mauro Suffritti, Medolla (IT); Stefano Ganzerli, Medolla (IT); Fabrizio Molducci, San Felice sul Panaro (IT); Paola Crivellari, Casumaro (IT); Alfonso Vollono, Medolla (IT); Marisa Torrini, San Felice sul Panaro (IT); Sonja Bellini, San Felice sul Panaro (IT); Mauro Gusella, Castelvetro di Modena (IT)

(73) Assignee: Gambro Lundia AB, Lund (SE)

( * ) Notice: Subject to any disclaimer, the term of this patent is extended or adjusted under 35 U.S.C. 154(b) by 663 days.

(21) Appl. No.: 17/925,070

(22) PCT Filed: May 17, 2021

(86) PCT No.: PCT/EP2021/062970
§ 371 (c)(1),
(2) Date: Nov. 14, 2022

(87) PCT Pub. No.: WO2021/239489
PCT Pub. Date: Dec. 2, 2021

(65) Prior Publication Data
US 2023/0181803 A1 Jun. 15, 2023

(30) Foreign Application Priority Data
May 29, 2020 (EP) ..................................... 20177592

(51) Int. Cl.
*A61M 1/16* (2006.01)
*A61M 1/34* (2006.01)

(52) U.S. Cl.
CPC ........ *A61M 1/1656* (2013.01); *A61M 1/3462* (2013.01); *A61M 1/3437* (2014.02)

(58) Field of Classification Search
CPC .............. A61M 1/3607; A61M 1/1603; A61M 1/361; A61M 1/342; A61M 1/3424; A61M 1/1656; A61M 1/3458; A61M 1/3462
See application file for complete search history.

(56) References Cited

U.S. PATENT DOCUMENTS 5,295,505 A 3/1994 Polaschegg et al.
5,344,231 A 9/1994 Jonsson et al.
(Continued)

FOREIGN PATENT DOCUMENTS

CN 107666919 2/2018
EP 0278100 8/1988
(Continued)

OTHER PUBLICATIONS

Chinese Office Action, Application No. 202180039025.0; Issuing No. 2025050701711050 dated May 7, 2025—17 pages.
(Continued)

*Primary Examiner* — Catharine L Anderson
*Assistant Examiner* — Eric Rassavong
(74) *Attorney, Agent, or Firm* — K&L Gates LLP

(57) ABSTRACT
An apparatus for extracorporeal blood treatment comprising a filtration unit, a blood circuit comprising a blood withdrawal line and a blood return line, and a fluid circuit. The fluid circuit comprises at least one or more water inlet ducts for receiving water, a dialysis preparation assembly comprising one or more concentrated sources housing a respective concentrate solution and configured to prepare a mixed solution of a dialysis fluid, wherein the water inlet duct is configured to provide water to the dialysis preparation assembly for preparing said mixed solution of dialysis fluid.
(Continued)

The fluid circuit further comprises an infusion preparation assembly comprising one or more concentrated sources housing a respective concentrate solution and configured to prepare a mixed solution of an infusion fluid, wherein the water inlet duct is configured to provide water to the infusion preparation assembly for preparing said mixed solution of infusion fluid.

25 Claims, 5 Drawing Sheets

(56) References Cited

U.S. PATENT DOCUMENTS

| | | | |
|---|---|---|---|
| 5,460,446 | A | 10/1995 | Chevallet et al. |
| 5,578,233 | A | 11/1996 | Giovanni |
| 6,635,026 | B1 | 10/2003 | Bernard |
| 6,793,827 | B1 | 9/2004 | Bosetto et al. |
| 9,220,830 | B2 | 12/2015 | Fontanazzi et al. |
| 10,434,236 | B2 | 10/2019 | Rovatti et al. |
| 11,376,354 | B2 * | 7/2022 | Nilsson ............... A61M 1/3607 |
| 2001/0037968 | A1 | 11/2001 | Bernard |

| | | | | |
|---|---|---|---|---|
| 2011/0105981 | A1 * | 5/2011 | Wagner ................ | A61M 60/113 604/29 |
| 2015/0343129 | A1 * | 12/2015 | Surace ................ | A61M 1/1603 604/6.09 |

FOREIGN PATENT DOCUMENTS

| | | | | |
|---|---|---|---|---|
| EP | 0401130 | 12/1990 | | |
| EP | 1904120 | 4/2008 | | |
| EP | 3505199 | 7/2019 | | |
| WO | 0074833 | 12/2000 | | |
| WO | 2012127298 | 9/2012 | | |
| WO | WO-2012127298 A1 * | 9/2012 | .......... | A61M 1/3441 |
| WO | 2018095691 | 5/2018 | | |

OTHER PUBLICATIONS

Chinese Search Report, Application No. 202180039025.0; Issuing No. 2025050701711050 dated May 7, 2025—2 pages.
EP Search Report—Application No. 20177592.1 mailing date Nov. 20, 2017—8 pages.
International Search Report—International Application No. PCT/EP2021/062970 mailing date Jul. 26, 2021—4 pages.
Written Opinion—International Application No. PCT/EP2021/062970 mailing date Jul. 26, 2021—7 pages.

* cited by examiner

WATER
DIALYSIS FLUID
INFUSION FLUID
BLOOD

APPARATUS FOR EXTRACORPOREAL BLOOD TREATMENT

PRIORITY CLAIM

The present application is a National Phase of International Application No. PCT/EP2021/062970, filed May 17, 2021, which claims priority to EP Application Serial No. 20177592.1, filed May 29, 2020, the entire contents of each of which are incorporated herein by reference and relied upon.

FIELD OF THE INVENTION

The present invention relates to an apparatus for extracorporeal blood treatment configured, and a method aimed, to prepare a mixed solution of dialysis fluid to be provided to a dialyzer and a mixed solution of infusion fluid to be infused into the blood circuit of a patient. Both the mixed solutions of dialysis fluid and infusion fluid are prepared by mixing a concentrate solution/s of a substance/s with water, the latter being provided from an on-line source. In one embodiment, the present invention may be used to deliver acetate-free biofiltration treatments with a constant or variable potassium management.

BACKGROUND OF THE INVENTION

The kidneys fulfil many functions, including the removal of water, the excretion of catabolites (or waste from the metabolism, for example urea and creatinine), the regulation of the concentration of the electrolytes in the blood (e.g. sodium, potassium, magnesium, calcium, bicarbonates, phosphates, chlorides) and the regulation of the acid/base equilibrium within the body, which is obtained in particular by the removal of weak acids and by the production of ammonium salts. In individuals who have lost the use of their kidneys, since these excretion and regulation mechanisms no longer work, the body accumulates water and waste from the metabolism and exhibits an excess of electrolytes. In order to overcome renal dysfunction, resort is conventionally made to a blood treatment involving extracorporeal circulation within a blood circuit through an exchanger having a semipermeable membrane (dialyzer) in which the patient's blood is circulated on one side of the membrane and a dialysis liquid, comprising the main electrolytes of the blood in concentrations close to those in the blood of a healthy subject, is circulated on the other side. The patient is connected to the extracorporeal blood circuit through a withdrawal (or arterial) and a return (or venous) line, the latter having respective needles at the end portions. A pressure difference is created between the two compartments of the dialyzer which are delimited by the semipermeable membrane, so that a fraction of the plasma fluid passes by ultrafiltration through the membrane into the compartment containing the dialysis liquid. The blood treatment which takes place in a dialyzer as regards waste from the metabolism and electrolytes results from two mechanisms of molecular transport through the membrane between the blood and the dialysis fluid. The dialysis fluid is prepared upstream of the dialyzer by mixing pure water with a plurality of predetermined substances, such as electrolytes, to be exchanged within the dialyzer with the patient's blood. Water comes from an inlet port receiving purified and de-ionized water (e.g., by reverse osmosis), to be subsequently further filtered within the apparatus so that a substantially endless water source is provided to the blood treatment apparatus. Treatment apparatuses configured to deliver hemofiltration or hemodiafiltration treatments also comprise an infusion line connected to the blood circuit of the dialysis disposable set: the infusion line may be used for infusing replacement fluid into the patient extracorporeal blood and/or to infuse one or more specific substances to control blood parameters. For example, a bicarbonate solution may be infused into the blood circuit for controlling blood acid-base balance of the patient during a dialysis treatment: a bag containing a bicarbonate liquid solution is usually provided to be connected to the blood circuit in order to allow a controlled infusion. For example, U.S. Pat. No. 5,578,223 discloses a dialysis apparatus wherein a fresh dialysis fluid not including any bicarbonate solution is routed towards the dialyzer (or alternatively into post infusion in the patient extracorporeal blood). A further post infusion line is provided for connection to an infusion solution contained in a respective bag. The infusion solution is a sodium bicarbonate solution. The apparatus control unit is configured to automatically regulate post infusion flow rate based on bicarbonate concentration in the infusion bag, desired concentration of bicarbonate into the patient and the effluent flow rate. During the extracorporeal blood treatment, the operators have to manage the bags, i.e. providing adequate installation on the apparatus scales, replacement of empty bags with new bags during treatment, handling of exhaust and new bags. Notably, new bicarbonate bags are somehow heavy (5/10 litres), which implies difficulties during installation on the machine scales: moreover, the liquid volume is limited, in order to reduce weight due to the necessity of manual handling, which in turn implies periodical replacement operations. To at least partially fix some issues of the prior art, document US20010037968 discloses a dialysis apparatus with an on-line dialysis fluid preparation and further including a post infusion line from a container. The on-line preparation section receives water and provides metered mixing of a first and a second concentrate with water. The control unit with the aid of two conductivity meters controls the proper conductivity of the dialysis fluid before directing it to the dialyzer. The control unit is further programmed to control concentrate mixing and infusion rate from the bag in order to achieve concentration targets into the blood of the patient for two different ionic substances, namely sodium and potassium. According to what described above, further prior art describes on-line preparation section for dialysis machines. For example, document U.S. Pat. No. 5,344,231 is directed to an apparatus for the preparation of dialysis fluids starting from a source of pure water. Water is taken from an inlet of a main preparation line and is sent through conduits to a powder cartridge. When the cartridge is filled and the proper solution containing the solutes is ready to be mixed for dialysis liquid preparation, the solution is injected into a main line leading to an inlet of the dialyzer. A recirculation circuit is also provided including a mixing vessel, a recirculation pump, a conductivity meter, and a number of cartridges for one or more powder or liquid-based concentrates. These concentrates are electrolytes including NaCl, KCl, CaCl and MgCl. The recirculation pump determines the water to pass through one of the cartridges: when the desired conductivity is reached, the next cartridge may be sequentially connected. Water from the source passes also through another powder cartridge to prepare another mixing solution subsequently injected into the main line, in which the concentration is checked by means of a conductivity meter and leaded to the dialyzer. Document U.S. Pat. No. 6,793,827 describes a similar system configured for profiling potassium concentration during the treatment; EP278100, U.S. Pat. No. 5,460,446 and EP401130 show other on-line preparation circuits. Document WO0074833A1 is directed to a centralized bicarbonate mixing system connected to a plurality of dialysis machines. The system includes a source of purified water, a mixing tank, an eductor having a hopper for receiving dry (powder) bicarbonate material, a mixing pump and a mixing conduit loop connecting the mixing pump, the eductor and the mixing tank so that as water is circulated in the mixing circuit, dry bicarbonate material is drawn into the educator and mixed with the water. A transfer conduit is provided so that a mixed bicarbonate solution can be transferred from the mixing conduit loop to the circulation tank. A circulation supply conduit connects the circulation tank so that mixed bicarbonate solution can be pumped from the circulation tank to the dialysis machines. Notably, the described circuit is arranged upstream with respect to the dialysis machines, wherein the latter are not described.

SUMMARY OF THE INVENTION

The aim of this invention is therefore to at least partially solve one or more of the drawbacks and/or limitations affecting the previous solutions.

An aim of embodiments of the present description is providing an extracorporeal blood treatment apparatus able to reduce servicing operations provided by an operator during a blood treatment session, i.e. to reduce or avoid need of periodical bag replacements.

It is a goal of embodiments of the present description to provide a dialysis apparatus configured to improve the treatment opportunities allowing to control and/or profile several blood parameters (e.g., pH, ionic substance concentration, etc. . . . ) independent one from the others, at the same time limiting the operator interventions on the dialysis machine. In this respect a further aim of embodiments of the present invention is providing an extracorporeal blood treatment apparatus able to automatically prepare, within the apparatus itself, mixing solutions of different dialysis and infusion fluids.

A further aim of embodiments of the present description is providing an extracorporeal blood treatment apparatus able to internally on-line prepare a mixed solution for infusion into a patient in order to control blood acid-base balance.

A further aim of embodiments of the present description is providing an extracorporeal blood treatment apparatus able to reduce or avoid the need of periodical replacements of the bicarbonate liquid solution bags provided for blood acid-base balance control.

A further aim of embodiments of the present description is providing an extracorporeal blood treatment apparatus able to increase safety during a blood treatment session, i.e. reduce risk of blood contamination due replacement of a liquid solution bag or the risks of treatment stops due to an empty bag during a treatment.

A 1st aspect is directed to an apparatus (1) for extracorporeal blood treatment comprising:

a filtration unit (2) having a primary chamber (3) and a secondary chamber (4) separated by a semi-permeable membrane (5);

a blood circuit (17) comprising at least:

a blood withdrawal line (6) extending between a first end connected to an inlet of the primary chamber and a second end for connection to a patient (P); and a blood return line (7) extending between a first end connected to an outlet of the primary chamber (3) and a second end for connection to said patient (P);

a fluid circuit (32) comprising at least:

one or more water inlet ducts (14a) for receiving water;

a dialysis preparation assembly (9) comprising one or more concentrated sources (27, 28) housing a respective concentrate solution and configured to prepare a mixed solution of a dialysis fluid, at least one of said one or more water inlet ducts (14a) being configurable to provide water to the dialysis preparation assembly (9) for preparing said mixed solution of dialysis fluid, an infusion preparation assembly (108), separate and distinct from the dialysis preparation assembly (9), comprising one or more concentrated sources (102) housing a respective concentrate solution (103) and configured to prepare a mixed solution of an infusion fluid, at least one of said one or more water inlet ducts (14a) being configurable to provide water to the infusion preparation assembly (108) for preparing said mixed solution of infusion fluid, intercepting elements arranged and operative at least on the fluid circuit (32) and configured to move at least between a closed position, wherein a fluid passage is interdicted, and an open position wherein fluid passage is allowed;

a control unit (12) configured to control one or more of said intercepting elements between the closed and open position to determine a fluid flow configuration defined in terms of fluid paths, said fluid flow configuration comprising at least a main operative mode wherein:

at least one of said one or more water inlet ducts (14a) is configured to provide water to the dialysis preparation assembly (9) for preparing said mixed solution of dialysis fluid and the mixed solution of dialysis fluid is suppliable to an inlet of the secondary chamber (4) of the filtration unit (2), and at least one of said one or more water inlet ducts (14a) is configured to provide water to the infusion preparation assembly (108) for preparing said mixed solution of infusion fluid and the mixed solution of infusion fluid is infusible through an infusion access point (19) into the blood circuit (17), in particular into the blood return (7) line of the blood circuit (17).

A $2^{nd}$ aspect is directed to a method for extracorporeal blood treatment comprising the following steps:

providing an apparatus comprising:

a filtration unit (2) having a primary chamber (3) and a secondary chamber (4) separated by a semi-permeable membrane (5);

a blood circuit (17) comprising at least:

a blood withdrawal line (6) extending between a first end connected to an inlet of the primary chamber and a second end for connection to a patient (P); and a blood return line (7) extending between a first end connected to an outlet of the primary chamber (3) and a second end for connection to said patient (P);

a fluid circuit (32) comprising at least:

one or more water inlet ducts (14a) for receiving water;

a dialysis preparation assembly (9) comprising one or more concentrated sources (27, 28) housing a respective concentrate solution and configured to prepare a mixed solution of a dialysis fluid, at least one of said one or more water inlet ducts (14*a*)
being configurable to provide water to the dialysis
preparation assembly (9) for preparing said mixed
solution of dialysis fluid, an infusion preparation assembly (108), separate and
distinct from the dialysis preparation assembly
(9), comprising one or more concentrated sources
(102) housing a respective concentrate solution
(103) and configured to prepare a mixed solution
of an infusion fluid, said at least at least one of said
one or more water inlet ducts (14*a*) being config-
urable to provide water to the infusion preparation
assembly (108) for preparing said mixed solution
of infusion fluid, intercepting elements arranged and operative at least on
the fluid circuit (32) and configured to move at least
between a closed position, wherein a fluid passage is
interdicted, and an open position wherein fluid pas-
sage is allowed;

determining a fluid flow configuration defined in terms of
fluid paths by controlling said intercepting elements
between the closed and open positions, said fluid flow
configuration comprising at least a main operative
mode wherein:

at least one of said one or more water inlet ducts (14*a*)
is configured to provide water to the dialysis prepa-
ration assembly (9) for preparing said mixed solution
of dialysis fluid and the mixed solution of dialysis
fluid is suppliable to an inlet of the filtration unit (2)
and, and at least one of said one or more water inlet ducts (14*a*)
is configured to provide water to the infusion prepa-
ration assembly (108) for preparing said mixed solu-
tion of infusion fluid and the mixed solution of
infusion fluid is infusible through an infusion access
into the blood circuit (17), in particular into the blood
return (7) line of the blood circuit (17);

wherein the method includes the following steps in the
main operative mode:

feeding water to the dialysis preparation assembly (9);
preparing said mixed solution of dialysis fluid;
supplying the mixed solution of dialysis fluid to an inlet
of the filtration unit (2);
feeding water to the infusion preparation assembly (108);
preparing said mixed solution of infusion fluid;
infusing the mixed solution of infusion fluid through an
infusion access into the blood circuit (17), in particular
into the blood return (7) line of the blood circuit (17).

In particular it is noted that, according to any one of the
1$^{st}$ and the 2$^{nd}$ aspect, the steps of supplying the mixed
solution of dialysis fluid and of infusing the mixed solution
of infusion fluid are simultaneous; in the main operative
mode, the dialysis fluid and the infusion fluid are not mixed
and routed independently. In a 3$^{rd}$ aspect according to any
one of the preceding aspects, in the main operative mode:

an outlet of the dialysis preparation assembly (9) is fluidly
connected to the inlet of the secondary chamber (4) of
the filtration unit (2), and/or an outlet of the infusion preparation assembly (108) is
fluidly connected to the blood circuit (17), in particular
fluidly connected to the blood return line (7) of the
blood circuit (17).

In a 4$^{th}$ aspect according to any one of the preceding
aspects, the apparatus comprises a supply line (8) extending
between an outlet of the dialysis preparation assembly (9)
and the inlet of the secondary chamber (4) of the filtration
unit (2).

In a 5$^{th}$ aspect according to any one of the preceding
aspects, the apparatus comprises an infusion line (109)
extending between an outlet of the infusion preparation
assembly (108) and the infusion access point (19) of the
blood circuit (17), in particular between an outlet of the
infusion preparation assembly (108) and the access point
(19) arranged on the blood return line (7) of the blood circuit
(17).

In a 6$^{th}$ aspect according to any one of the preceding
aspects, said infusion access point (19) of the blood circuit
(17) is at an air separator configured to remove gases from
the fluid and/or blood before being infused into the patient.

In a 7$^{th}$ aspect according to any one of the preceding
aspects, the one or more water inlet ducts (14*a*) are config-
ured to supply water to both the dialysis preparation assem-
bly (9) and the infusion preparation assembly (108).

In an 8$^{th}$ aspect according to any one of the preceding
aspects, in the main operative mode, the one or more water
inlet ducts (14*a*) are configured to supply water indepen-
dently and, through different tube segments, directly to both
the dialysis preparation assembly (9) and the infusion prepa-
ration assembly (108).

In a 9$^{th}$ aspect according to any one of the preceding
aspects, the control unit (12) is configured to control the
dialysis preparation assembly (9) and the infusion prepara-
tion assembly (108) to respectively prepare the mixed solu-
tion of dialysis fluid and the mixed solution of infusion fluid
so that the mixed solution of dialysis fluid is different in
composition from the mixed solution of infusion fluid, in
particular the dialysis fluid is different from the infusion
fluid based on:

a nature of one or more solutes; and/or
a concentration of one or more solutes.

In a 10$^{th}$ aspect according to any one of the preceding
aspects, in the main operative mode:

the mixed solution of dialysis fluid is supplied to the inlet
of the secondary chamber (4) of the filtration unit (2)
simultaneously to the infusion of the mixed solution of
infusion fluid into the blood circuit (17), in particular
wherein the infusion fluid is not routed to the secondary
chamber (4) of the filtration unit (2) and in particular
the dialysis fluid is not infused into the blood circuit
(17).

In a 11$^{th}$ aspect according to any one of the preceding
aspects, in the main operative mode the dialysis fluid and the
infusion fluid are respectively routed to the secondary cham-
ber (4) of the filtration unit (2) and to the blood circuit (17)
without being mixed together.

In a 12$^{th}$ aspect according to any one of the preceding
aspects, the fluid circuit (32) comprises a first preparation
line (9*a*) and a second preparation line (108*a*), the first
preparation line (9*a*) being distinct from the second prepa-
ration line (108*a*).

In a 13$^{th}$ aspect according to the preceding aspect:
the dialysis preparation assembly (9) comprises the first
preparation line (9*a*), and
the infusion preparation assembly (108) comprises the
second preparation line (108*a*);
both the first preparation line (9*a*) and the second prepa-
ration line (108*a*) being connected individually to the water
inlet duct (14*a*), in particular said water inlet duct being
arranged upstream with respect to both said first and second
preparation lines (9*a*, 108*a*).

In a 14$^{th}$ aspect according to any one of the two preceding
aspects, the first preparation line (9*a*) and the second preparation line (108a) define together, at least in the main operation mode, fluidly independent branches of the fluid circuit (32).

In a 15$^{th}$ aspect according to any one of the preceding aspects, in the main operation mode the mixed solution of infusion fluid is not mixed up with the mixed solution of dialysis fluid at least within the fluid circuit (32).

In a 16$^{th}$ aspect according to any one of the preceding aspects, the fluid flow configuration further comprises a second operative mode wherein:

the mixed solution of infusion fluid and the mixed solution of dialysis fluid are mixed up defining an auxiliary mixed solution of dialysis fluid in particular flowing in the supply line (8);

and optionally wherein:

the auxiliary mixed solution of dialysis fluid is suppliable to the inlet of the secondary chamber (4) of the filtration unit (2); and/or the auxiliary mixed solution of dialysis fluid is infusible into the blood circuit (17), in particular wherein the control unit is configured to define the second operative mode of the fluid flow configuration by controlling the intercepting elements to put the infusion preparation assembly (108) in fluid communication with the dialysis preparation assembly (9) to obtain the auxiliary mixed solution of dialysis fluid, in particular the control unit controlling the intercepting elements to fluidly connect the infusion preparation assembly (108) in series with the dialysis preparation assembly (9).

In a 17$^{th}$ aspect according to the preceding aspect, in said second operative mode the dialysis preparation assembly (9) is fluidly connected in series, in particular upstream or downstream, with respect to the infusion preparation assembly (108).

In an 18$^{th}$ aspect according to any one of the two preceding aspects, in said second operative mode the first preparation line (9a) is fluidly connected in series, in particular upstream or downstream, with respect to the second preparation line (108a).

In a 19$^{th}$ aspect according to any one of the three preceding aspects, in the second operative mode the dialysis preparation assembly (9) is fluidly connected downstream to the infusion preparation assembly (108).

In a 20$^{th}$ aspect according to any one of the preceding aspects, said fluid flow configuration further comprises a third operative mode wherein:

the mixed solution of infusion fluid and the mixed solution of dialysis fluid are mixed up defining an auxiliary mixed solution of dialysis fluid flowing in the supply line (8);

the auxiliary mixed solution of dialysis fluid is suppliable to the inlet of the secondary chamber (4) of the filtration unit (2);

optionally the auxiliary mixed solution of dialysis fluid is infusible into the blood circuit (17).

In a 21st aspect according to the preceding aspect, in said third operative mode, the dialysis preparation assembly (9) is fluidly connected in parallel with respect to the infusion preparation assembly (108).

In a 22$^{nd}$ aspect according to any one of the two preceding aspects, in said third operative mode the first preparation line (9a) is fluidly connected in parallel with respect to the second preparation line (108a).

In a 23$^{rd}$ aspect according to any one of the three preceding aspects, in the third operative mode, the outlet of the first preparation line (9a) is fluidly connected to the outlet of the second preparation line (108a), said outlets infusing into the supply line (8).

In a 24$^{th}$ aspect according to any one of the preceding aspects, the one or more concentrated sources (27, 28) of the dialysis preparation assembly (9) comprise at least one concentrated substance in the group between sodium chloride, calcium chloride, magnesium chloride, potassium chloride.

In a 25$^{th}$ aspect according to any one of the preceding aspects, at least one concentrated solution (103) housed into the one or more concentrated sources (102) of the infusion preparation assembly (108) comprises a buffer substance, in particular at least one in the group between bicarbonate, citrate, lactate and acetate, in particular bicarbonate powder.

In a 26$^{th}$ aspect according to any one of the preceding aspects, in the main operative mode, the at least one concentrated solution (103) housed into the one or more concentrated sources (102) of the infusion preparation assembly (108) comprises bicarbonate, in particular sodium bicarbonate such as dry sodium bicarbonate.

In a 27$^{th}$ aspect according to any one of the preceding aspects, in the main operative mode, the at least one concentrated solution (103) housed into the one or more concentrated sources (102) of the infusion preparation assembly (108) comprises sodium, in particular dry sodium in the form of dry sodium bicarbonate or dry sodium chloride.

In a 28$^{th}$ aspect according to any one of the preceding aspects, in the main operative mode, one of the one or more concentrated sources (27, 28) of the dialysis preparation assembly (9) comprises concentrated electrolytes, including sodium, calcium and potassium and optionally magnesium.

In a 29$^{th}$ aspect according to any one of the preceding aspects, in the main operative mode, one of the one or more concentrated sources (27, 28) of the dialysis preparation assembly (9) comprises glucose and optionally citrate.

In a 30$^{th}$ aspect according to any one of the preceding aspects, in the main operative mode, another one of the one or more concentrated sources (27, 28) of the dialysis preparation assembly (9) comprises concentrated electrolytes, including sodium and calcium and optionally magnesium.

In a 31$^{st}$ aspect according to any one of the preceding aspects, the potassium concentration in the one of the one or more concentrated sources (27, 28) is different from the potassium concentration in the another one of the one or more concentrated sources (27, 28), in particular the another one of the one or more concentrated sources (27, 28) containing no potassium.

In a 32$^{nd}$ aspect according to any one of the preceding aspects, the concentrations of the other electrolytes different from potassium is equal in the one of the one or more concentrated sources (27, 28) and in the another one of the one or more concentrated sources (27, 28).

In a 33$^{rd}$ aspect according to any one of the preceding aspects, in the main operative mode, the another one of the one or more concentrated sources (27, 28) of the dialysis preparation assembly (9) comprises glucose and optionally citrate.

In a 34$^{th}$ aspect according to any one of the preceding aspects from 16 to 33, in the second operative mode, the at least one concentrated solution (103) housed into the one or more concentrated sources (102) of the infusion preparation assembly (108) comprises sodium, in particular dry sodium in the form of dry sodium bicarbonate or dry sodium chloride.

In a 35$^{th}$ aspect according to any one of the preceding aspects from 16 to 34, in the second operative mode, the at least one concentrated solution (103) housed into the one or more concentrated sources (102) of the infusion preparation assembly (108) comprises bicarbonate, in particular sodium bicarbonate such as dry sodium bicarbonate.

In a 36th aspect according to any one of the preceding aspects from 16 to 35, in the second operative mode, one of the one or more concentrated sources (27, 28) of the dialysis preparation assembly (9) comprises concentrated electrolytes, including calcium and potassium and optionally magnesium.

In a 37th aspect according to any one of the preceding aspects from 16 to 36, in the second operative mode, one of the one or more concentrated sources (27, 28) of the dialysis preparation assembly (9) comprises glucose and optionally citrate.

In a 38th aspect according to any one of the preceding aspects, one of the one or more concentrated sources (27, 28) of the dialysis preparation assembly (9) comprises the following components:

sodium
potassium,
calcium,
magnesium,
citrate,
glucose

In a 39th aspect according to the preceding aspect, when said components are diluted in the fluid flowing in the first preparation line, the components are in within the following concentration ranges in mmol/l:

| sodium | 0 or 120-170 mmol/l |
|---|---|
| potassium, | 0-9 mmol/l |
| calcium, | 1-3 mmol/l |
| magnesium, | 0.2-0.6 mmol/l |
| citrate, | 0-2 mmol/l |
| glucose | 0-10 mmol/l | in particular wherein, sodium is optional, but when present is in the range between 120-170 mmol/l. In a 40th aspect according to any one of the preceding aspects, the components, when diluted in the fluid flowing in the first preparation line (9a), are within the following concentration ranges in mmol/l:

| sodium | 0 or 130-160 mmol/l |
|---|---|
| potassium, | 0-8 mmol/l |
| calcium, | 1-2.5 mmol/l |
| magnesium, | 0.3-0.6 mmol/l |
| citrate, | 0-1.5 mmol/l |
| glucose | 0-6 mmol/l | in particular wherein, sodium is optional, but when present is in the range between 130-160 mmol/l. In a 41st aspect according to any one of the preceding aspects, the at least one concentrated solution (103) housed into the one or more concentrated sources (102) of the infusion preparation assembly (108) comprises the following components:

sodium,
bicarbonate wherein, when diluted in the fluid flowing in the second preparation line (108a), the components are in within the following concentration ranges in mmol/l:

| sodium, | 120-170 mmol/l |
|---|---|
| bicarbonate | 20-40 mmol/l |

In a 42nd aspect according to any one of the preceding aspects, when diluted in the fluid flowing in the second preparation line (108a), the components are in within the following concentration ranges in mmol/l:

| sodium, | 130-160 mmol/l |
|---|---|
| bicarbonate | 24-38 mmol/l |

In a 43rd aspect according to any one of the preceding aspects, the one or more water inlet ducts (14a) are configured to receive water from a depuration system arranged upstream, said depuration system being configured to provide the water inlet duct with purified water, in particular distilled water.

In a 44th aspect according to any one of the preceding aspects, the apparatus comprises a conductivity sensor (35) arranged in the dialysis preparation assembly (9), in particular on the first preparation line (9a), downstream with respect to the one or more concentrated sources (27, 28) and configured to provide a signal representative of an electrical conductivity of the mixed solution of dialysis fluid, optionally to provide a signal representative of an electrical conductivity of the auxiliary mixed solution of dialysis fluid, the control unit (12) being configured to receive said conductivity signal.

In a 45th aspect according to the preceding aspect, the control unit (12) is configured to receive the signal representative of the electrical conductivity to determine the actual conductivity and to compare the actual conductivity to a target conductivity.

In a 46th aspect according to the preceding aspect, the control unit is configured to drive the dialysis preparation assembly (9) to reduce a difference between the actual conductivity and the target conductivity.

In a 47th aspect according to any one of the preceding aspects, the apparatus comprises a flow meter (41) arranged on the supply line (8) and configured to provide a signal representative of a flow rate of the mixed solution of dialysis fluid, optionally of the auxiliary mixed solution of dialysis fluid, the control unit (12) being configured to receive said flow rate signal.

In a 48th aspect according to any one of the preceding aspects, the apparatus comprises a dialysis fluid pump (25) arranged on the supply line (8) and configured to determine a flow rate of the mixed solution of dialysis fluid, optionally of the auxiliary mixed solution of dialysis fluid.

In a 49th aspect according to the preceding aspect, the control unit (12) is configured to control said dialysis fluid pump (25), in particular the control unit being configured to control start, stop and speed of the fluid pump (25).

In a 50th aspect according to any one of the preceding aspects, the apparatus comprises a conductivity sensor (104) arranged in the infusion preparation assembly (108), in particular on the second preparation line (108a), downstream with respect to the one or more concentrated sources (102) of the infusion preparation assembly (108) and configured to provide a signal representative of an electrical conductivity of the mixed solution of infusion fluid, the control unit (12) being configured to receive said conductivity signal.

In a 51st aspect according to the preceding aspect, the control unit (12) is configured to receive the signal representative of the electrical conductivity to determine the actual conductivity and to compare the actual conductivity to a target conductivity.

In a 52nd aspect according to any one of the preceding aspects, the control unit is configured to drive the infusion preparation assembly (108) to reduce a difference between the actual conductivity and the target conductivity.

In a 53rd aspect according to any one of the preceding aspects, the apparatus comprises a flow meter (105) arranged in the infusion preparation assembly (108), in particular on the second preparation line (108a), and configured to provide a signal representative of a flow rate of the mixed solution of infusion fluid, the control unit (12) being configured to receive said flow rate signal.

In a 54th aspect according to any one of the preceding aspects, the apparatus comprises an infusion pump (106,111) arranged on the second preparation line (108a) and configured to determine a flow rate of the mixed solution of infusion fluid, the control unit (12) being configured to control said infusion pump (106, 111), in particular the control unit being configured to control start, stop and speed of the infusion pump (106, 111).

In a 55th aspect according to any one of the preceding aspects, the fluid circuit (32) comprises at least one infusion ultrafilter (107), in particular a first and a second infusion ultrafilters (107a, 107b) arranged in series, located on the infusion line (109) and configured to provide a filtration of the mixed solution of infusion fluid.

In a 56th aspect according to any one of the preceding aspects, the concentrated source (102) of the infusion preparation assembly (108) comprises a reservoir housing the concentrated substance (103), said concentrated substance (103) comprising bicarbonate, in particular bicarbonate powder.

In a 57th aspect according to any one of the preceding aspects, said intercepting elements comprise at least an inlet valve (34) arranged on the first preparation line (9a), said inlet valve being interposed between the water inlet duct (14a) and the one or more concentrated sources (27, 28) of the dialysis preparation assembly (9).

In a 58th aspect according to any one of the preceding aspects, said intercepting elements comprise at least an inlet valve (100a) arranged on the second preparation line (108a), said inlet valve being interposed between the water inlet duct (14a) and the one or more concentrated sources (102) of the infusion preparation assembly (108).

In a 59th aspect according to any one of the preceding aspects, the fluid circuit (32) comprises a bridging line (110) interposed in fluid connection between the infusion line (109) and the supply line (108).

In a 60th aspect according to the preceding aspect, said intercepting elements comprises a bridging valve (110a) arranged on the bridging line (110) to allow or interdict fluid flow between the infusion line (109) and the supply line (108).

In a 61st aspect according to any one of the preceding aspects, said intercepting elements comprise an infusion valve (109a) arranged on the infusion line (109) to allow or prevent the infusion fluid to flow towards the access point (19).

In a 62nd aspect according to any one of the preceding aspects, in the main operation mode the inlet valves (34, 100a) of the first and second preparation lines (9a, 108a) are in the open position.

In a 63rd aspect according to any one of the preceding aspects, in the main operation mode the bridging valve (110a) is in the closed position.

In a 64th aspect according to any one of the preceding aspects, in the main operation mode the dialysis fluid pump

(25) determines dialysis fluid flow towards the secondary chamber (4) of the filtration unit (2).

In a 65th aspect according to any one of the preceding aspects, in the main operation mode the infusion pump (106) of the infusion line (109) determines infusion fluid flow towards the access point (19) of the blood circuit (17) or directly in a vascular access of the patient.

In a 66th aspect according to any one of the preceding aspects from 16 to 65, in the second operation mode the inlet valve (34) of the first preparation line (9a) is in the closed position.

In a 67th aspect according to any one of the preceding aspects from 16 to 66, in the second operation mode the inlet valve (100a) of the second preparation line (108a) is in the open position.

In a 68th aspect according to any one of the preceding aspects from 16 to 67, in the second operation mode the bridging valve (110a) is in the open position.

In a 69th aspect according to any one of the preceding aspects from 16 to 68, in the second operation mode the dialysis fluid pump (25) determines dialysis fluid flow towards the secondary chamber (4) of the filtration unit (2).

In a 70th aspect according to any one of the preceding aspects from 16 to 69, in the second operation mode the infusion pump (106) of the infusion line (109) is not active.

In a 71st aspect according to any one of the preceding aspects, the apparatus comprises a graphical user interface (22) operatively connected to the control unit (12) and configured to receive, from a user, one or more inputs to select at least one between the main operation mode and the second operation mode (and optionally the third operation mode).

In a 72nd aspect according to any one of the preceding aspects at least one concentrated source (28) of the concentrated sources (27, 28) of the dialysis preparation assembly (9) comprises a concentrated solution of potassium, In a 73rd aspect according to the preceding aspect, the dialysis fluid preparation assembly (9) comprises a delivery line (37) fluidly connecting said concentrated source (28) including potassium to the first preparation line (9a) and a concentrate pump (30) arranged on said delivery line (37), wherein said concentrate pump (30) of the dialysis fluid preparation assembly (9) is configured to deliver a predetermined flow rate of the concentrated solution of potassium into the first preparation line (9a).

In a 74th aspect according to any one of the preceding aspects, the other concentrated source (27) of the concentrated sources (27, 28) of the dialysis preparation assembly (9) comprises a concentrated solution with no potassium or with a concentration of potassium different from the concentration of potassium in the concentrated source (28), the dialysis fluid preparation assembly (9) comprising a delivery line (36) fluidly connecting said concentrated source (27) to the first preparation line (9a) and a concentrate pump (29) arranged on said delivery line (36).

In a 75th aspect according to the preceding aspect, said concentrate pump (29) of the dialysis fluid preparation assembly (9) is configured to deliver a predetermined flow rate of the concentrated solution into the first preparation line (9a), the control unit (12) being configured to drive said concentrate pumps (29, 30) to deliver a constant or profiled amount of potassium to obtain a set concentration value or a set concentration profile along time of potassium in the dialysis fluid.

In a 76th aspect according to any one of the preceding aspects the control unit (12) is configured to command the dialysis preparation assembly (9) to obtain a predetermined potassium concentration value into the mixed solution of the dialysis fluid.

In a 77th aspect according to any one of the preceding aspects, the potassium concentration value is constant or variable during the blood treatment according to a predetermined potassium profiling curve.

In a 78th aspect according to any one of the preceding aspects, the control unit (12) is configured to vary the potassium concentration in the mixed solution of dialysis fluid during the blood treatment according to a potassium profiling curve, in particular said profiling curve presenting a decreasing potassium concentration over time.

In a 79th aspect according to the preceding aspect, the potassium profiling curve is according to the following formula:

$$K(t) = K_{INI} + (K_F - K_{INI}) \cdot \left( \frac{t - T_{delay}}{T_{dialysis} - T_{delay}} \right)^{0.5}$$

where $T_{delay} < t < T_{dialysis}$ wherein:

K(t) is an actual value of potassium concentration in the mixed solution of dialysis fluid;

$K_{ini}$ is an initial value of potassium concentration in the mixed solution of dialysis fluid;

$K_F$ is a final value of potassium concentration in the mixed solution of dialysis fluid;

$T_{delay}$ is an initial time delay of the potassium delivery start;

$T_{dialysis}$ is the length of the blood treatment;

t is the current treatment time.

In an 80th aspect according to any one of the preceding aspects, in the main operation mode, a conductivity value of the mixed solution of dialysis fluid does not directly affect a conductivity value of the mixed solution of infusion fluid.

In an 81st aspect according to any one of the preceding aspects, the apparatus comprises a blood pump (21) operative on the blood circuit (17), in particular on the blood withdrawal line (6) of the blood circuit (17).

In an 82nd aspect according to any one of the preceding aspects, the fluid circuit (32) includes one water inlet duct (14a) for receiving water, said inlet duct (14a) branching into a water line (100) to feed water directly to the infusion fluid preparation assembly (108) and into a water branch (113) to feed water directly to the dialysis fluid preparation assembly (9).

In an 83rd aspect according to the preceding aspect, the intercepting elements comprise one or more valves (100a, 34) to allow or prevent water from flowing in the water line (100) and/or in the water branch (113), in particular said intercepting elements including an inlet valve (100a) upstream the infusion fluid preparation assembly (108) to allow or prevent fluid from flowing inside the water line (100) and an inlet valve (34) upstream the dialysis fluid preparation assembly (9) to allow or prevent fluid from flowing inside the water branch (113).

In an 84th aspect according to any one of the preceding aspects, in the main operating mode, the control unit (12) drives the one or more valves (100a, 34) to allow water flow towards both the dialysis fluid preparation assembly (9) through the water branch (113) and the infusion preparation assembly (108) through the water line (100).

In an 85th aspect according to any one of the preceding aspects, fluid circuit (32) includes a bridging line (110) fluidly connecting an outlet of the infusion fluid preparation assembly (108) with an inlet to the dialysis fluid preparation assembly (9), wherein intercepting elements comprises one or more valves (110a) to allow or prevent water from flowing in the bridging line (110).

In an 86th aspect according to any one of the preceding aspects, in the main operating mode, the control unit (12) drives the one or more valves (110a) to prevent fluid flow through the bridging line (110) between the outlet of the infusion preparation assembly (108) and the inlet of the dialysis fluid preparation assembly (9).

In an 87th aspect according to any one of the preceding aspects, the fluid circuit (32) comprises an infusion line (109) connected to an outlet of the infusion preparation assembly (108) routing the infusion fluid to the blood circuit (17).

In an 88th aspect according to any one of the preceding aspects, the fluid circuit (32) comprises a supply line (8) connected to an outlet of the dialysis preparation assembly (9) routing the infusion fluid to the filtration unit (2).

In an 89th aspect according to any one of the preceding aspects, the fluid circuit (32) comprises a connecting line (114) fluidly connecting the infusion line (109) and the supply line (8), the intercepting elements comprises one or more valves (114a, 114b) to allow or prevent fluid from flowing in the connecting line (114).

In an 89ath aspect according to the preceding aspect, the connecting line (114) is connected to the infusion line (109) at a branch point interposed between the infusion pump (106) and the infusion ultrafilter (107).

In an 89bth aspect according to the two preceding aspects, the connecting line (114) is connected to the supply line (8) at a branch point placed downstream of the dialysis fluid preparation assembly (9).

In a 90th aspect according to the three preceding aspects, in the main operating mode, the control unit (12) drives the one or more valves (114a, 114b) to prevent fluid flow through the connecting line (114) between the infusion line (109) and the supply line (8).

In a 91st aspect according to any one of the preceding aspects, the fluid circuit (32) comprises an infusion line (109) connected to an outlet of the infusion preparation assembly (108) routing the infusion fluid to the blood circuit (17), the infusion line including an on-line port (115) and a tube portion connecting the outlet of the infusion preparation assembly (108) to the on-line port (115).

In a 92nd aspect according to any one of the preceding aspects, the tube portion connecting the outlet of the infusion preparation assembly (108) to the on-line port (115) includes an infusion pump (106), in particular the infusion pump (106) being placed between the outlet of the infusion preparation assembly (108) and a connecting line (114) fluidly connecting the tube portion with an outlet of the dialysis preparation assembly (9).

In a 93rd aspect according to any one of the preceding aspects, the tube portion connecting the outlet of the infusion preparation assembly (108) to the on-line port (115) includes at least one infusion ultrafilter (107), in particular infusion ultrafilter (107) being placed between a connecting line (114) fluidly connecting the tube portion with an outlet of the dialysis preparation assembly (9) and the on-line port (115).

In a 94th aspect according to any one of the preceding aspects, the on-line port (115) is an access placed on an external portion of a cabinet of the apparatus, the online port (115) being configured for a connection of a disposable tubing directing fluid to the blood circuit (17).

In a 95$^{th}$ aspect according to any one of the preceding aspects, the fluid circuit (32) comprises a joining tubing (116) fluidly connecting the supply line (8) to the infusion line (109), in particular connecting the supply line (8) downstream an infusion pump (106) placed on the infusion line (109) and optionally connecting the supply line (8) downstream an infusion ultrafilter (107).

In a 96$^{th}$ aspect according to the preceding aspect, the intercepting elements comprises one or more valves (116a) to allow or prevent fluid from flowing in the joining tubing (116).

In a 97$^{th}$ aspect according to any one of the two preceding aspects, in the main operating mode, the control unit (12) drives the one or more valves (116a) to prevent fluid flow through the joining tubing (116) between the infusion line (109) and the supply line (8).

In a 98$^{th}$ aspect according to any one of the three preceding aspects, the joining tubing (116) connects the supply line (8) to an on-line port (115) of the infusion line (109).

In 99$^{th}$ aspect according to any one of the preceding aspects, the fluid circuit (32) includes one water inlet duct (14a) for receiving water, said inlet duct (14a) branching into a water line (100) to feed water directly to the infusion fluid preparation assembly (108) and into a water branch (113) to feed water directly to the dialysis fluid preparation assembly (9), wherein the fluid circuit (32) comprises an inlet flow meter (49) placed on the inlet duct (14a) upstream the branching and an effluent line flow meter (42) on the effluent line (13), wherein, at least in the main operating mode (and optionally also in the second and third operating modes), the control unit (12) receive signals from the inlet flow meter (49) and the effluent line flow meter (42) to control an ultrafiltration rate through the dialyzer.

In a 100$^{th}$ aspect according to any one of the preceding aspects, the control unit (12) receives or calculates a set ultrafiltration rate to be achieved during the extracorporeal blood treatment and drives the apparatus to achieve the set ultrafiltration rate based on the signals received from the inlet flow meter (49) and the effluent line flow meter (42), in particular based on a difference between an effluent flow rate (measured with the effluent line flow meter) and the sum of the infusion flow rate and the dialysis flow rate (measured with the inlet flow meter).

In a 101$^{st}$ aspect according to any one of the preceding aspects, the inlet flow meter (49) and the effluent line flow meter (42) are implemented with a differential flow meter.

In a 102$^{nd}$ aspect according to any one of the preceding aspects, the fluid circuit (32) comprises a supply line flow meter (41) on the supply line (8), an infusion line flow meter (105) on the infusion line (109) and an effluent line flow meter (42) on the effluent line (13), wherein, in the main operating mode, the control unit (12) receive signals from the supply line flow meter (41), the infusion line flow meter (105) and the effluent line flow meter (42) to control an ultrafiltration rate through the dialyzer.

In a 103$^{th}$ aspect according to any one of the preceding aspects, the control unit (12) receives or calculates a set ultrafiltration rate to be achieved during the extracorporeal blood treatment and drives the apparatus to achieve the set ultrafiltration rate based on the signals received from the supply line flow meter (41), the infusion line flow meter (105) and the effluent line flow meter (42), in particular based on a difference between an effluent flow rate and the sum of the infusion flow rate, measured with the infusion line flow meter (105), and the dialysis flow rate.

In a 104$^{th}$ aspect according to any one of the preceding aspects, the supply line flow meter (41) and the effluent line flow meter (42) are implemented with a differential flow meter.

In a 105$^{th}$ aspect according to any one of the preceding aspects, the control unit (12) is configured to control the one or more of said intercepting elements between the open and closed position to allow or prevent the infusion line (109) to be in fluid communication with the supply line (8).

In a 106$^{th}$ aspect according to any one of the preceding aspects, the fluid circuit (32) defines a fluid line net comprising the dialysis preparation assembly (9), the infusion preparation assembly (108), the infusion line (109), the supply line (8) and the intercepting elements, wherein the dialysis preparation assembly (9), the infusion preparation assembly (108), the infusion line (109), and the supply line (8) are connected each other through said fluid line net and fluidly connectable each other based on the open or position of the intercepting elements, in particular the control unit being configured to control the intercepting elements to define different flow paths within the fluid circuit (32).

In a 107$^{th}$ aspect according to any one of the preceding aspects, the control unit (12) is configured to control the one or more of said intercepting elements between the open and closed position to allow or prevent the dialysis preparation assembly (9) to be in fluid communication with the infusion preparation assembly (108).

In a 108$^{th}$ aspect according to any one of the preceding aspects, the dialysis preparation assembly (9) and the infusion preparation assembly (108) are connected each other through fluid lines defining a fluid line net comprising the intercepting elements, the control unit (12) being configured to control the one or more of said intercepting elements between the open and closed position to define two or more fluid paths for the mixed solution of dialysis fluid and for the mixed solution of infusion fluid.

In a 109$^{th}$ aspect according to the preceding aspect, said two or more fluid paths comprise at least one fluid path wherein a fluid, in particular the mixed solution of dialysis fluid, prepared by the dialysis preparation assembly (9) is not mixed with a fluid, in particular the mixed solution of infusion fluid, prepared by the infusion preparation assembly (108) and one further fluid path wherein either:

the fluid prepared by the dialysis preparation assembly (9) enters into the infusion preparation assembly (108);

the fluid prepared by the infusion preparation assembly (108) enters into the dialysis preparation assembly (9);

the fluid prepared by the dialysis preparation assembly (9) is mixed with the fluid prepared by the infusion preparation assembly (108).

In a 110$^{th}$ aspect according to any one of the preceding aspects, said fluid flow configuration comprising at least a second operative mode wherein the dialysis preparation assembly (9) and the infusion preparation assembly (108) cooperate to prepare an auxiliary mixed solution of dialysis fluid, in particular different from the mixed solution of dialysis fluid and from the mixed solution of infusion fluid.

In a 111$^{th}$ aspect according to any one of the preceding aspects, said fluid flow configuration comprising at least a second operative mode wherein the control unit is configured to control the intercepting elements to mix the mixed solution of dialysis fluid with the mixed solution of infusion fluid defining an auxiliary mixed solution of dialysis fluid.

In a 112$^{th}$ aspect according to any one of the preceding aspects, the control unit (12) is configured to control the one or more of said intercepting elements between the open and closed position to allow or prevent the dialysis preparation assembly (9) to be in fluid communication with the infusion preparation assembly (108), in particular to allow or prevent the mixed solution of dialysis fluid prepared in the dialysis preparation assembly (9) to be in fluid communication with the infusion preparation assembly (108), or the mixed solution of infusion fluid prepared in the infusion preparation assembly (108) to be in fluid communication with the dialysis preparation assembly (9).

DRAWINGS

Some embodiments and some aspects of the invention will be described below with reference to the attached drawings, provided for illustrative purposes only, wherein.

DEFINITIONS

In this detailed description, corresponding parts illustrated in the various figures are indicated with the same numerical references. The figures may illustrate the invention through non-scale representations; therefore, parts and components illustrated in the figures relating to the object of the invention may relate exclusively to schematic representations.
Upstream and/Downstream The terms upstream and downstream refer to a direction or trajectory of advancement of a fluid, in particular blood in the blood circuit and dialysis/infusion fluid in the dialysis/infusion line/s, during normal use of the apparatus, wherein the fluid is configured to flow along the fluid line during an extracorporeal blood treatment.

DETAILED DESCRIPTION

Blood Treatment Apparatus 1

Figure 1:
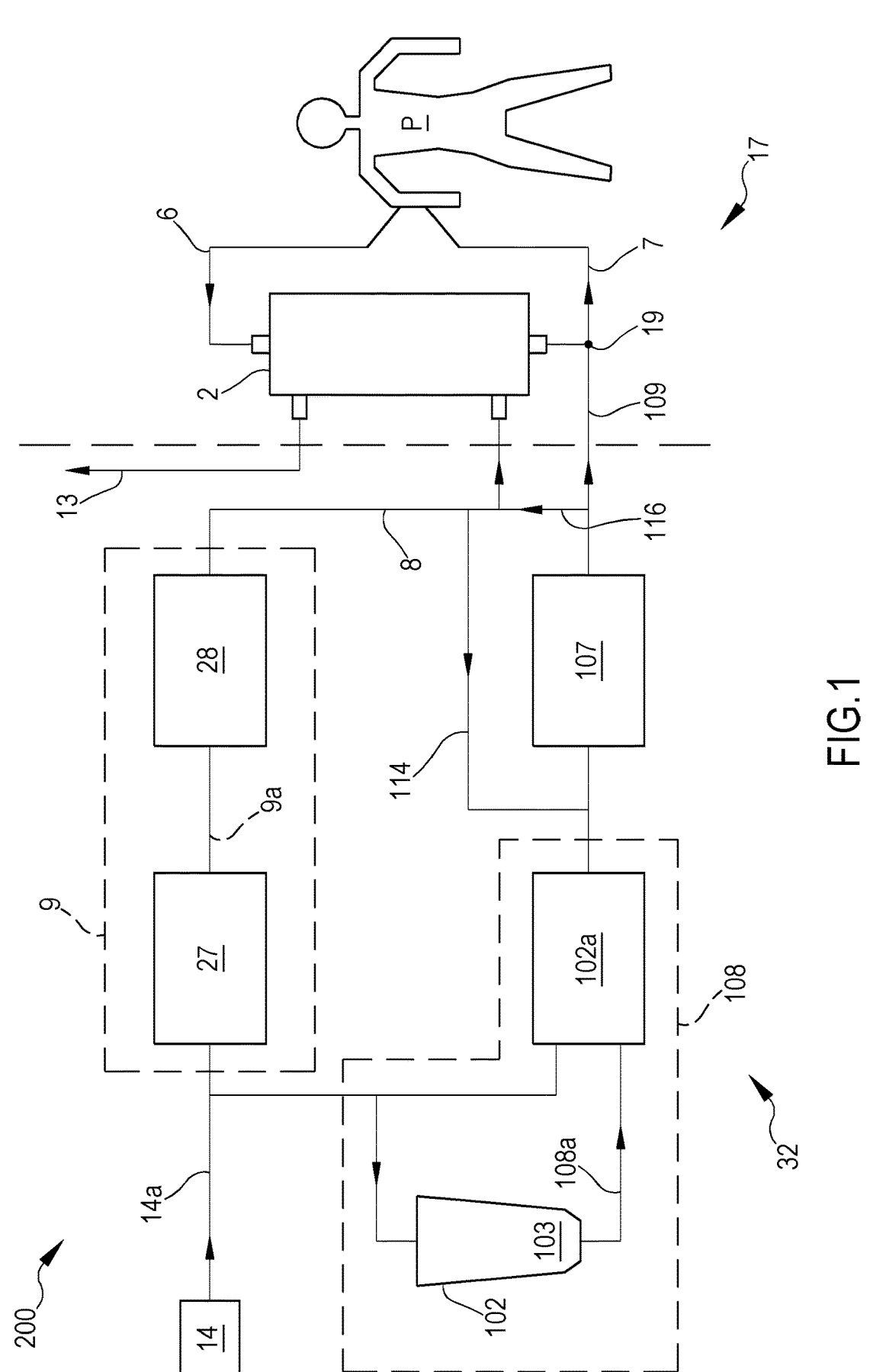
FIG. 1 is a schematic view of a blood treatment apparatus according to an embodiment of the present description.
Figure 2:
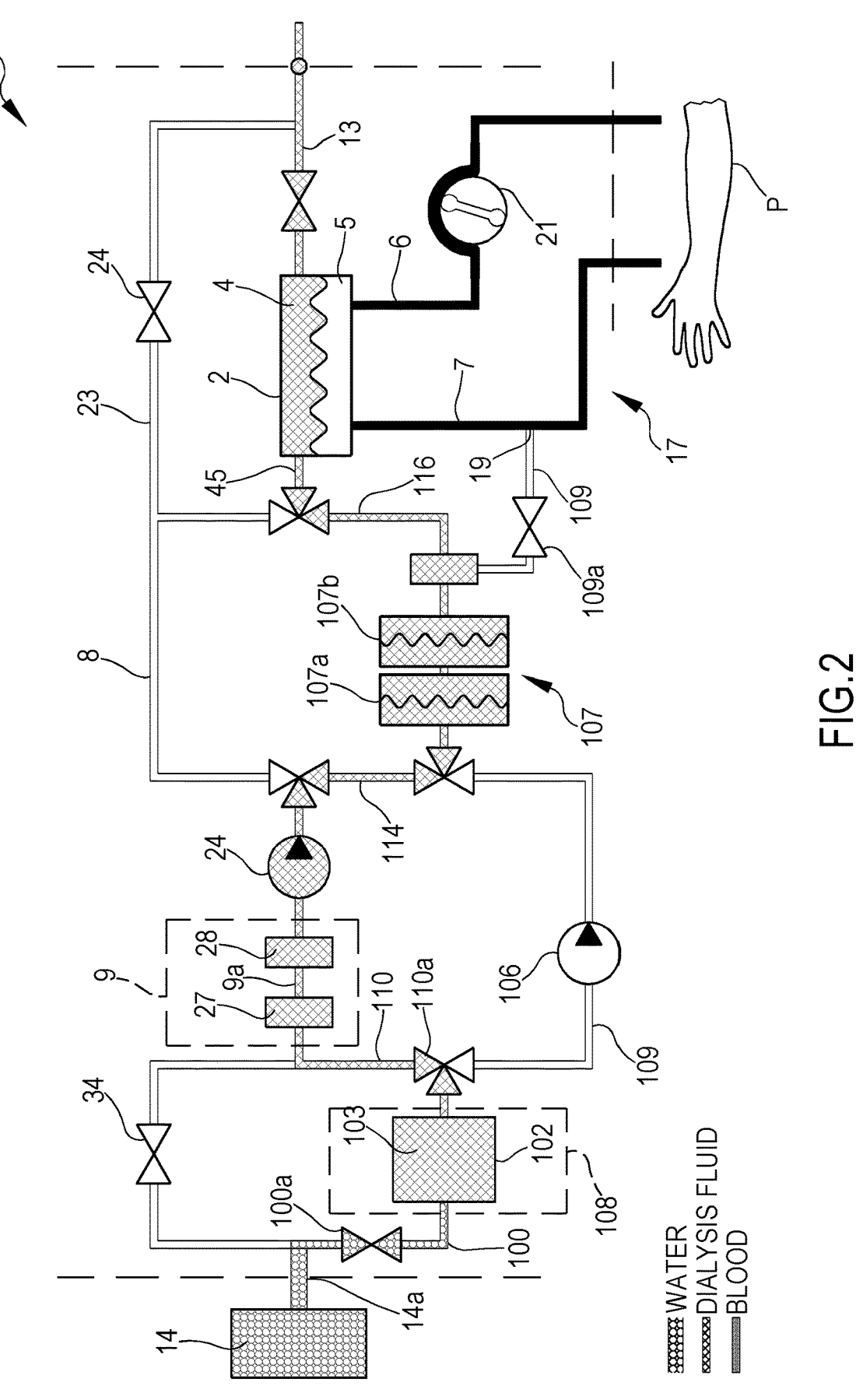
FIGS. 2 and 3 are schematic views of fluid path configurations of a blood treatment apparatus according to an embodiment of the present description.
Figure 3:
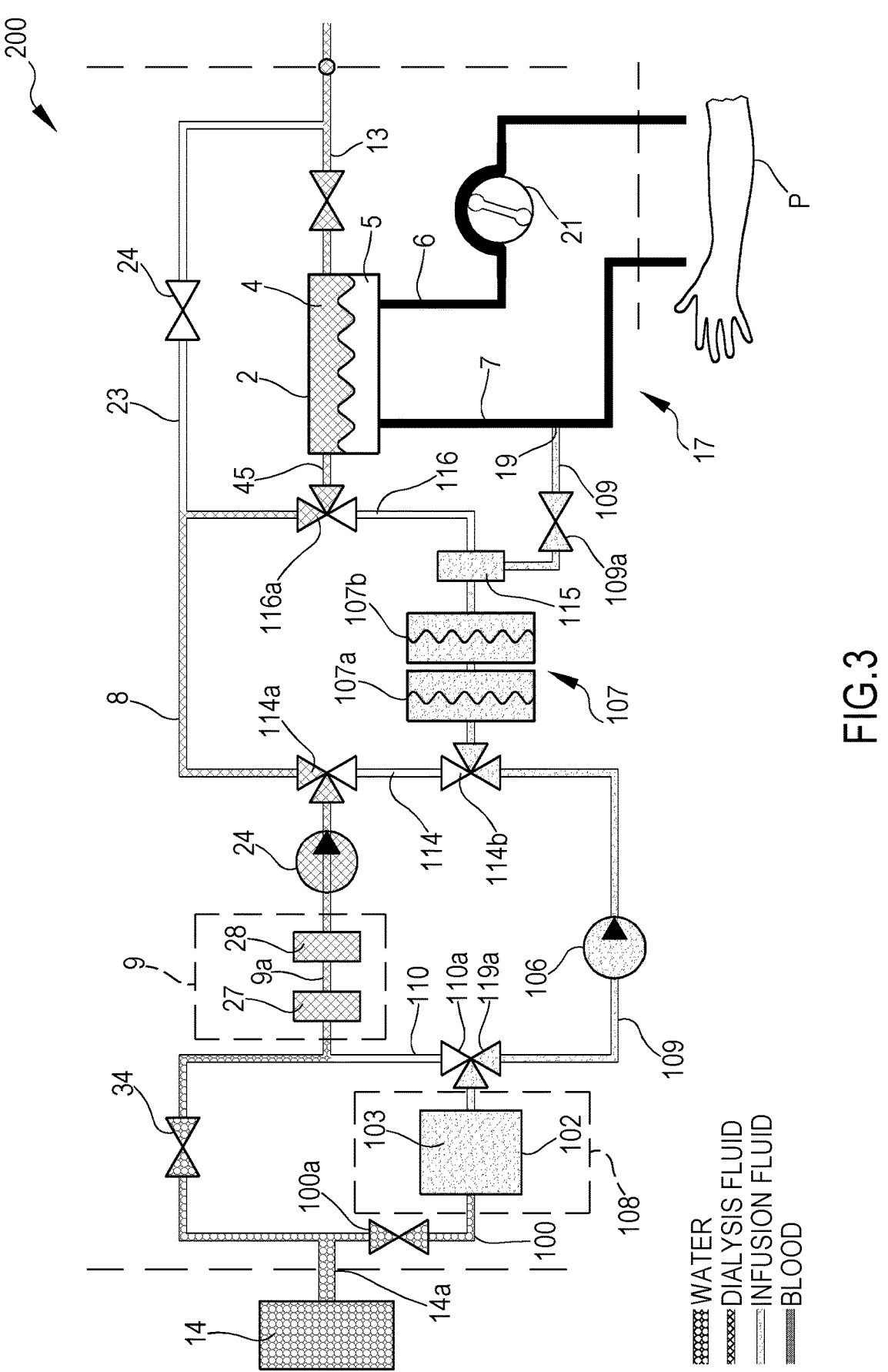
Figure 4:
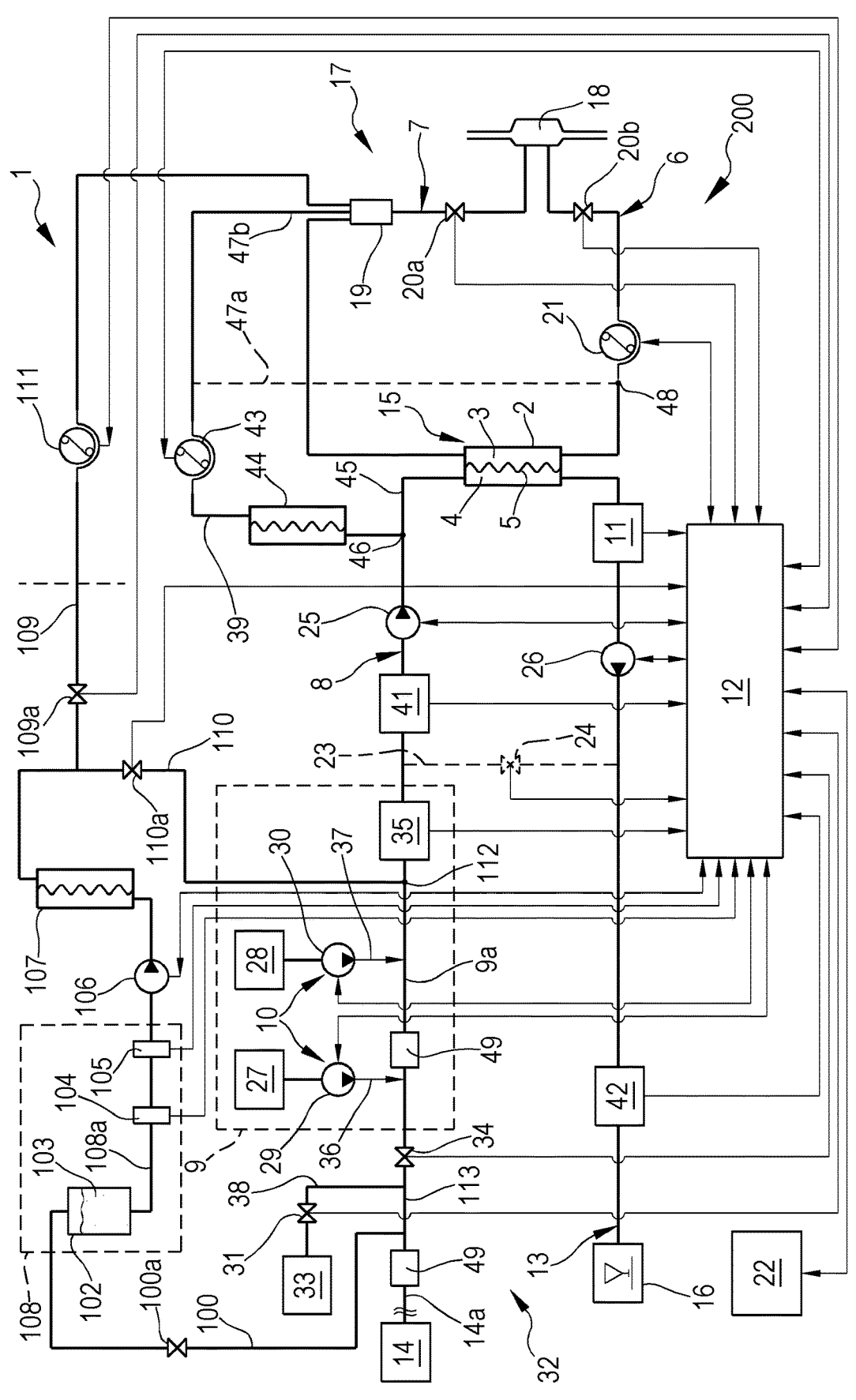
FIG. 4 is a more detailed schematic view of a blood treatment apparatus according to an embodiment of the present description.

FIG. 4 illustrates an extracorporeal blood treatment apparatus 1 according to a generic embodiment. An example of a hydraulic circuit 200 is also schematically illustrated in FIG. 4, but it is to be noted that the specific structure of the hydraulic circuit 200 is not relevant for the purposes of the present invention and therefore other circuits different to those specifically shown in FIG. 4 might be used in consequence of the functional and design needs of each single medical apparatus. FIGS. 1, 2 and 3 also show slightly different embodiments of the hydraulic circuit 200 according to simplified schemes, in order to highlight the main components of the hydraulic circuit of the present disclosure in one or more operative configurations.

The hydraulic circuit 200 exhibits a dialysis fluid circuit 32 presenting at least one dialysis fluid supply line 8. Usually, the dialysis fluid supply line 8 is the tubing where the dialysis fluid being prepared flows, namely the main line receiving water and concentrate (or concentrates) infusion and routing the prepared dialysis fluid towards the filtration unit and/or a direct infusion into the extracorporeal blood circuit. Depending on the apparatus treatment mode, the dialysis fluid supply line 8 may or, may not, assume different hydraulic circuit line configurations. In a hemodialysis (HD)

treatment mode, the supply line 8 is destined to transport a dialysis fluid from a dialysis preparation assembly 9 towards a treatment station 15 where one or more filtration units 2, or dialyzers, operate. Dialysis fluid and blood exchange through a semipermeable membrane 5 in the filtration unit 2 mainly by diffusion process. In a hemofiltration (HF) treatment mode, the supply line 8 comprises an auxiliary infusion line 39, which is destined to transport fluid from the supply line 8 to the blood circuit: in particular the auxiliary infusion line 39 is connected to the supply line at a branch point 46, and to the blood circuit at an access point 19, the latter being for example placed in correspondence of an an air separator configured to remove gases from the blood before infusion. The auxiliary infusion line 39 may include an ultrafilter 44 to additionally filter the received fluid upstream the access point 19 into the blood circuit. The removal of waste products from the blood is achieved by using large amounts of ultrafiltration with simultaneous reinfusion of sterile replacement fluid in the blood circuit. In a hemodiafiltration (HDF) treatment mode, the supply line 8 is destined to transport the dialysis fluid from the dialysis preparation assembly 9 towards the treatment station 15 and also comprises the auxiliary infusion line 39 to transport the fluid to the blood circuit 17. HDF is a combination of hemodialysis and hemofiltration. Notwithstanding the fact that different fluid circuits 32 may be used to deliver HF, HD and HDF treatments e.g., having exclusively the relevant lines for the predetermined treatment (e.g. no auxiliary infusion line 39 for HD, no inlet line 45 for HF), generally the fluid circuit 32 is of the kind shown in FIG. 4 and includes both the auxiliary infusion line 39 connected to the blood circuit and an inlet line 45 connected to an inlet of the filtration unit 2, wherein an apparatus control unit 12 may then control the passage of fluid trough said lines, depending on the selected treatment, through e.g. proper intercepting elements, such as valves or clamps.

The dialysis fluid circuit 32 further comprises at least one dialysis effluent line 13, destined for the transport of a dialysate liquid (spent dialysate and liquid ultrafiltered from the blood through a semipermeable membrane 5) from the treatment station 15 towards an evacuation zone, schematically denoted by reference number 16 in FIG. 4. The fluid circuit 32 cooperates with a blood circuit 17, also schematically represented in FIG. 4 in its basic component parts. The specific structure of the blood circuit is also not fundamental, with reference to the present invention. Thus, with reference to FIG. 4, a brief description of a possible embodiment of a blood circuit is made, which is however provided purely by way of non-limiting example. The blood circuit 17 of FIG. 1 comprises a blood withdrawal line 6 designed to remove blood from a vascular access 18 and a blood return line 7 designed to return the treated blood to the vascular access 18. The blood circuit 17 of FIG. 4 further comprises a primary chamber 3, or blood chamber, of the blood filtration unit 2, while a secondary chamber 4 of the blood filtration unit 2 is connected to the supply line 8. In greater detail, the blood withdrawal line 6 is connected at the inlet of the primary chamber 3, while the blood return line 7 is connected at the outlet of the primary chamber 3. In an embodiment, the blood return line 7 and/or the blood withdrawal line 6 are part of a disposable set: the lines may be made of transparent material, i.e. plastic or PVC or silicone, so that a fluid flowing inside the lines might be visible from the outside.

In turn, the dialysis fluid supply line 8 is connected at the inlet of the secondary chamber 4, while the dialysis effluent line 13 is connected at the outlet of the secondary chamber 4.

The filtration unit 2, for example a dialyzer or a plasma filter or a hemofilter or a hemodiafilter, comprises, as mentioned, the two chambers 3 and 4 which are separated by a semipermeable membrane 5, for example of the hollow-fiber type or plate type.

The blood circuit 17 may also comprise one or more air separators 19: in particular, as shown in FIG. 4, the apparatus may comprise an air separator 19 on the blood return line 7. An auxiliary air separator on the blood withdrawal line 7 may also be provided.

The apparatus further comprises safety clamps 20*a*, 20*b* arranged close to the vascular access 18 of the patient: in particular the apparatus may comprise a blood return safety clamp 20*a* and a blood withdrawal safety clamp 20*b* respectively arranged on the blood return line 7 and on the blood withdrawal line 6. According to a blood flow direction, assumed during a dialysis treatment, from the blood withdrawal line 6, through the filter unit 2 and towards the blood return line 7, the blood return safety clamp 20*a* is arranged downstream with respect to the air separator 19 of the blood return line 7. The safety clamps 20*a*, 20*b* may be activated by a control unit 12 (and/or manually) to close, for example for safety reasons, the blood return line 7 and the blood withdrawal line 6 when the vascular access 18 has to be isolated.

The extracorporeal blood treatment apparatus 1 may also comprise one or more blood pumps 21, for example positive displacement pumps such as peristaltic pumps, arranged on the blood circuit 17: in the example of FIG. 4, a blood pump 21 is arranged on the blood withdrawal line 6, in particular interposed between the filter unit 2 and the vascular access 18. In a further embodiment, more than one blood pump 21 may be arranged on the blood circuit 17, for example a first blood pump may be arranged on the withdrawal line 6 and a second blood pump may be arranged on the return line 7. The blood return line 7 extends between a first end, connected to the outlet of the primary chamber 3 of the filtration unit 2, and a second end for connection to the patient: analogously, the blood withdrawal line 6 extends between a first end, connected to the inlet of the primary chamber 3 of the filtration unit 2, and a second end for connection to the patient.

The apparatus of above-described embodiment also comprises the control unit 12, i.e. a programmed/programmable control unit, and a user interface 22 (e.g. a graphic user interface or GUI) connected to the control unit 12 in order to allow a user to command one or more treatment operations or to visualize on a screen one or more parameters related to the blood treatment. The control unit 12 may, for example, comprise one or more digital microprocessor units or one or more analog units or other combinations of analog units and digital units. Relating by way of example to a microprocessor unit, once the unit has performed a special program (for example a program coming from outside or directly integrated on the microprocessor card), the unit is programmed, defining a plurality of functional blocks which constitute means each designed to perform respective operations as better described in the following description.

In combination with one or more of the above characteristics, the medical apparatus may also comprise a closing/bypass device operating in the dialysis fluid circuit 32 and commendable between one first operating condition, in which the closing device allows a liquid to flow towards the filtration unit 2, and a second operative position, in which the closing device blocks the passage of liquid towards the filtration unit 2. In this case, the control unit 12 may be connected to the closing device and programmed to drive the closing device to pass from the first to the second operative condition, should an alarm condition have been detected. The closing device may comprise a bypass line 23 which connects the dialysis fluid supply line 8 and the dialysate effluent line 13 bypassing the dialyzer, and one or more fluid check members 24 connected to the control unit 12 for selectively opening and closing the bypass line 23. The components (bypass line 23 and fluid check members 24) are represented by a broken line in FIG. 4. The check members 24 on command of the control unit close the fluid passage towards the treatment zone and connect supply line 8 directly with the dialysis effluent line 13 through the bypass line 23.

Again with the aim of controlling the fluid passage towards the filtration unit 2, a dialysis fluid pump 25 and a dialysate pump 26 may be provided and located respectively on the dialysis fluid supply line 8 and on the dialysate effluent line 13 and also operatively connected to the control unit 12.

The apparatus further comprises one or more water inlet ducts 14*a* for receiving water from a water source 14: the water source 14 may comprise a depuration system (e.g., a RO system) arranged upstream with respect to the water inlet duct 14*a* and configured to provide the water inlet duct with purified water, in particular distilled/sterile water. In other terms, the inlet ducts 14*a* are configured to be connected to the running water network (supplying i.e. tap water which is in turn filtered by the depuration system) which is able to provide a continuous and substantially endless amount of water. Notably, the water source 14 does not actually belongs to the apparatus 1, being the latter configured to be connected to the water source 14 through the water inlet duct 14*a*. Inlet water quality should normally be compliant with ISO 13959 standard.

Although the apparatus may comprise more than one inlet duct 14*a* aimed to receive the water, the apparatus, as shown in FIG. 4, may comprise one and only one single inlet duct 14*a* configured to be fluidly connected to the water source 14, so that water is supplied to the apparatus through this single inlet duct 14*a*. An intercepting element, such as a hydraulic valve, may be arranged at the beginning of the inlet duct 14*a* for safety reasons: this intercepting element is movable between a closed position wherein a water flow is prevented, and an open position wherein the water flow is allowed.

The apparatus 1 comprises intercepting elements arranged and operative at least on the fluid circuit 32 which are connected to the control unit 12 in turn configured to move a single or a plurality of intercepting elements independently between the open and the closed position. The intercepting elements may comprise clamps, acting i.e. externally of the fluid lines, or hydraulic valves acting though a shutter within the fluid flow. The intercepting elements described here after are according to the above described features.

The apparatus further comprises a dialysis fluid preparation assembly 9, fluidly interposed between the inlet duct 14*a* and the supply line 8, comprising one or more concentrated sources 27, 28 housing a respective concentrated solution and configured to prepare a mixed solution of a dialysis fluid. The water inlet duct 14*a* is configured to provide water to the dialysis preparation assembly 9 for preparing the mixed solution constituting the dialysis fluid: in particular the dialysis preparation assembly 9 is configured for mixing water, coming from the water duct 14, with the concentrate solutions of the sources 27, 28 to provide as outcome the mixed solution of dialysis fluid to the supply line 8. The dialysis fluid preparation assembly 9 comprises a first preparation line 9*a* fluidly interposed between the inlet duct 14*a* and the supply line 8 and configured to receive the concentrated solutions of the sources 27, 28 respectively through delivery lines 36, 37, the latter comprising in turn respective concentrate pumps 29, 30 configured to determine a flow of the concentrated substance from the concentrated sources to the first preparation line 9*a*. A flow rate sensor (not shown in the figures), connected to the control unit 12, may also be provided on the delivery line 36, 37 of the concentrated sources 27, 28 in order to monitor the amount of concentrated substance delivered to the first preparation line 9*a*.

In general, the first preparation line 9*a* includes one or more sensors configured to monitor a property of the fluid flowing along the line itself; the property is either conductivity of the fluid or concentration of an ionic substance. In more detail, usually a sensor 49 is present on the first preparation line 9*a* downstream the mixing point receiving the first delivery line 36; another sensor 35 is present on the first preparation line 9*a* downstream the mixing point receiving the second delivery line 37. Sensor 49 may measure conductivity of the fluid flowing in the first preparation line 9*a* after mixing with the first concentrate solution 27 and before receiving the second concentrate solution. The control unit 12 receives signals from the conductivity sensor 49 and may regulate concentrate pump 29 to properly adjust the infusion flow rate of the concentrate to reach the prescribed conductivity target. Similarly, sensor 35 may measure conductivity of the fluid flowing in the first preparation line 9*a* after mixing with the second concentrate solution 28. The control unit 12 receives signals from the conductivity sensor 35 and may regulate concentrate pump 30 to properly adjust the infusion flow rate of the concentrate to reach the prescribed conductivity target of the combined infusion from concentrates 27 and 28. An identical control routine may be performed using proper concentration sensors instead of conductivity sensors. As an alternative, just one sensor (in the present case sensor 35) downstream all infusion points may be used to control the overall conductivity of the dialysis fluid.

FIG. 4 shows two concentrated sources 27, 28 connected the first preparation line 9*a*: anyhow, in one embodiment, one single concentrate source may be used or, in another embodiment, additional concentrated sources housing respective concentrated solutions may be provided. Of course, if just one concentrate solution is used, one conductivity/concentration sensor only may be used. If more than two concentrates are used, one sensor downstream each mixing point may be used.

It is further noted that the preparation assembly may include a plurality of connections, lines and pumps respective for concentrates and that just one or a number less than the plurality of lines may be used.

According to a first general embodiment, the concentrated sources 27, 28 of the dialysis preparation assembly 9 comprise one or more concentrated substance in the group between sodium chloride, calcium chloride, magnesium chloride, potassium chloride, a buffer (e.g., bicarbonate) and other components such as citrate, glucose and acetate.

Normally, a concentrate container A (for example container 27) comprises the main electrolytes and a concentrate container B (for example container 28) includes sodium chloride and the buffer.

In one embodiment, one concentrate container 27; 28 includes a (e.g., liquid) concentrate comprising calcium chloride, magnesium chloride, potassium chloride, glucose and optionally citrate. After dilution into water, a solution including the following components is prepared:

| | | |
|---|---|---|
| $K^+$ | 0-5 (1-4)* | mmol/l |
| $Ca^{++}$ | 1.2-2 (1.4-1.8)* | mmol/l |
| $Mg^{++}$ | 0.3-0.7 (0.5)* | mmol/l |
| $Cl^-$ | 100-120 (107-112)* | mmol/l |
| Cit (opt) | 0-2 (1)* | mmol/l |
| Glucose/$C_6H_{12}O_6$ | 0-2 (0-1)* | mmol/l |

*narrower concentration ranges are between brackets.

The other concentrate container 28; 27 includes a (e.g., dry) concentrate comprising sodium bicarbonate. In case a powder concentrate is used in concentrate container B, then some water is spilled from the preparation line 9*a* (or from inlet 14*a*) to pre-dilute the concentrate allowing the concentrate pump to generate the concentrate flow. After dilution into the main preparation line 9*a*, the solution comprises sodium and bicarbonate ions, too. Sodium ions are in a range between 120 and 170 mmol/l, in particular between 120 and 160 mmol/(for example around 140 mmol/l). Bicarbonate ions are in a range between 20 and 40 mmol/l, in particular between 24 and 38 mmol/(for example around 34 mmol/l). Of course sodium concentration in the dialysis fluid may be set according to the patient prescription.

By mixing both concentrates A and B, a proper dialysis fluid is obtained for use in HD, HF and HDF treatments. Generally, the dialysis preparation assembly 9 prepares dialysis fluid "on-line" by infusing sodium chloride plus other ionic substances and a buffer into the first preparation line 9*a* in a proper ratio between each other.

In other terms, the dialysis fluid preparation assembly 9 is configured to perform an on-line dialysis fluid preparation by mixing water with a predetermined amount of concentrated substance(s). The expression "on-line" is directed to a fluid preparation wherein the water is supplied by a running water network able to provide a substantially endless amount of water (i.e. depurated water): therefore, the expression "on-line" is used to differentiate with respect to an embodiment wherein a ready-to-use dialysis bags or tanks, having a finite capacity, are used as treatment fluid sources.

The fluid circuit 32 further comprises an infusion preparation assembly 108, separate and distinct from the dialysis preparation assembly 9, comprising one or more concentrated sources 102 housing one or more respective concentrate solutions 103, as shown in FIG. 4. The concentrated sources 102 may comprise just one reservoir for housing the concentrated solution 103. The infusion preparation assembly 108, fluidly interposed between, and connected to, the inlet duct 14*a* and to an infusion line 109, is configured to prepare a mixed solution of an infusion fluid by mixing water supplied by the inlet duct 14*a* with the concentrated solution/s 103. The fluid prepared by the infusion preparation assembly 108 is denoted as "infusion fluid" to differentiate from the treatment fluid prepared by the dialysis preparation assembly 9, denoted as "dialysis fluid". However, the different names are used exclusively for sake of clarity in distinguishing the two different fluids, but do not imply that the "dialysis fluid" may not be infused into the blood circuit and that the "infusion fluid" may not be routed to the filtration unit second chamber 4.

Notwithstanding the fact that an embodiment of an infusion preparation assembly 108 different from the embodiment of the dialysis preparation assembly 9 is shown in the figures, it is noted that the arrangement of containers, fluid lines and concentrate pumps may be identical for both the preparation assemblies 9, 108. Since however the two preparation assemblies 9, 108 are independent one from the other and both controlled by the control unit 12 according to the treatment needs, different medical fluids may be prepared simultaneously, for example one for infusion into the blood circuit, the other for routing to the dialyzer. The medical fluids are both suitable to treat a patient (i.e., may be both infused into the extracorporeal blood and/or directed to the secondary chamber of the filtration unit to exchange with blood through the semipermeable membrane), but differs in their composition, in terms of solute nature and/or solute concentration/s. As represented in FIG. 4, the fluid circuit 32 may also be provided with an intercepting element 100*a*, namely an inlet valve 100*a*, i.e. a hydraulic valve or a clamp, connected to the control unit 12 and interposed between the infusion fluid preparation assembly 108 and the inlet duct 14*a*, so that a water flow towards the infusion fluid preparation assembly 108 is allowed or prevented.

According to the structure of the fluid circuit 32 described above, the water inlet duct 14*a* is configured to supply water independently to both the dialysis preparation assembly 9 and the infusion preparation assembly 108. In other terms, the water inlet duct 14*a* is configured to supply water independently to either/both the first or/and to the second preparation lines 9*a*, 108*a*: therefore, the first preparation line 9*a* and the second preparation line 108*a* define together fluidly independent branches of the fluid circuit 32 supplied by the same water source 14. Pure water enters into the infusion fluid preparation assembly 108.

The infusion fluid preparation assembly 108 comprises a second preparation line 108*a* wherein mixing of the concentrated solution 103 with water occurs.

As mentioned according to an embodiment not shown in the attached figures, the concentrated source 102 may be connected to the second preparation line 108*a* through a delivery line provided with a pump or with a delivery means connected to the control unit 12 and configured to provide a desired amount of concentrated substance into the second preparation line 108*a*. In other words, the pump or delivery means is configured to deliver a predetermined amount of concentrated solution 103 into the second preparation line 108*a* in order to prepare a mixed solution of infusion fluid having a desired concentration of the substance. Alternatively, as shown in FIG. 4, the water is supplied from the inlet duct 14*a* into the concentrated source 102 to obtain the mixed solution. In particular and in one embodiment, the concentrated solution 103 may be a concentrated solution of sodium bicarbonate, for example a sodium bicarbonate powder or sodium bicarbonate dry concentrate. In this configuration, water is fed to the powder solution to prepare a saturated bicarbonate solution (see FIG. 4 configuration). For example, a water branch may depart from water line 100 and enter into concentrate source 102 (embodiment shown in FIG. 1). An injection line and a corresponding pump (on tubing 108*a*) may then deliver a proper amount of saturated solution to the water line 100 or to a mixing chamber 102*a* (where also water line 100 has an inlet) so that any diluted solution of bicarbonate may be obtained flowing towards infusion line 109. As schematically shown in FIG. 1, the concentrated source 102 may be arranged in parallel to the second preparation line 108*a*, so that both an inlet and an outlet of the concentrated source 102 are fluidly connected to the second preparation line 108*a*. According to this embodiment, water is allowed to partly bypass the concentrated source 102, so that any variable substance concentration in the infusion fluid may be obtained. According to the embodiment shown in FIG. 1, a mixing chamber 102*a* may be provided on the second preparation line 108*a* downstream to the concentrated source 102 of the infusion fluid preparation assembly 108: the mixing chamber is configured to allow mixing of the concentrated solution 103, i.e. bicarbonate saturated solution, with the water supplied by the inlet duct 14. A conductivity sensor may also be provided within or downstream the mixing chamber 102*a* to provide a conductivity signal representative of the conductivity in the mixed solution representative of the substance concentration.

Alternatively, a concentrated liquid solution of (e.g., sodium) bicarbonate may be used. In this situation, no water branch may be necessary to generate a saturated liquid solution. The concentrated solution 102 may be properly metered through the respective pump along the injection line to the water line 100 (embodiment not shown). Further, the infusion preparation assembly 108 may have a configuration identical/similar to the configuration of the dialysis fluid preparation assembly 9 in terms of hydraulic circuit. In other words, more than one concentrate substance may be injected into the water line 100 to prepare a suitable infusion fluid. The difference will be the prepared treatment fluid, which will differ in composition with respect to the treatment fluid prepared with the dialysis fluid preparation assembly 9. It is noted that the same concentrate containers may eventually be mounted in the dialysis fluid preparation assembly 9 and in the infusion fluid preparation assembly 108; however, the control unit would drive the respective infusion pump/s differently, based on the prescription, so that fluids with different conductivities and/or different concentrations of predetermined substances (e.g., sodium and/or calcium and/or potassium and/or magnesium ions) will be produced ready for the subsequent use in treating the patient. Alternatively, concentrate containers with different substance concentrations may be used to prepare fluids with different proportions of the various substances. In more detail, the mixed solution of dialysis fluid is different in composition from the mixed solution of infusion fluid. The apparatus is therefore suitable for preparing on-line two different treatment fluids ready to be sent to the second chamber of the filtration unit and/or directly infused into the extracorporeal blood circuit.

Operating as above stated, allows to control substance infusion with additional freedom; thereby it is possible to e.g., set different targets for substance concentration within the patient blood (such as sodium concentration and potassium concentration) and reaching these independent targets at the end of the treatment by properly profiling the concentration of these substances in the dialysis fluid and in the infusion fluid.

Moving back to FIG. 4, the fluid circuit 32 may also comprise a sensor 104, in particular a conductivity sensor 104, arranged on the second preparation line 108*a* downstream to an outlet of the concentrated source 102: in particular the conductivity sensor 104 is configured to provide a signal representative of an electrical conductivity of the mixed solution of infusion fluid. The control unit 12 is connected to the conductivity sensor 104 and is configured to receive and elaborate said conductivity signal: in particular the control unit drives the infusion fluid preparation assembly 108 to prepare the mixed solution of infusion fluid on the basis of a comparison between a target conductivity value and an actual conductivity value of the infusion fluid measured by the conductivity sensor 104. Alternatively, the sensor 104 on the second preparation line 108*a* may differently include a concentration sensor (e.g., an ion selective sensor) configured for measuring the concentration of at least one substance in the infusion fluid, such as the sodium concentration. In this case, the control unit 12 may be configured to prepare the mixed solution of infusion fluid on the basis of a comparison between a target concentration value and an actual concentration value of the infusion fluid measured by the concentration sensor 104. Of course, in case more than one concentrate container is present, a (conductivity or concentration) sensor may be present at or downstream each mixing point.

The fluid circuit 32 may also comprise a flow meter 105 arranged on the second preparation line 108a downstream with respect to the concentrated source/s 102 of the infusion fluid preparation assembly 108 and configured to provide a signal representative of a flow rate of the mixed solution of infusion fluid. The control unit 12 is connected to the flow meter 105 and is configured to receive and elaborate said flow rate signal.

The fluid circuit 32 also comprises an infusion fluid pump 106, connected to the control unit 12, arranged on the infusion line 109 and configured to determine a flow rate of the infusion fluid. The control unit 12 is configured to control the start, stop and speed of the infusion fluid pump 106 so that a desired flow rate of infusion fluid is generated in the line. The control unit 12 may be also configured to control the infusion pump 106 to vary the flow rate as a function of at least one between the measured conductivity and flow rate signals relative to the mixed solution of infusion fluid and/or to the measured conductivity and flow rate signals relative to the mixed solution of dialysis fluid. The fluid circuit 32 may also comprise an infusion ultrafilter 107 arranged on the infusion line 109 between the infusion fluid preparation assembly 108 and the access 19, in particular downstream of the infusion pump 106 and the concentrate sources 102. In particular, the infusion ultrafilter 107 may comprise a first and a second infusion ultrafilters 107a, 107b, as shown in FIGS. 2 and 3, connected in series each other. The above mentioned infusion line 109 is fluidly connected to, and interposed between, an outlet of the infusion fluid preparation assembly 108 and the access point 19 of the blood circuit 17: the infusion line 109 is configured to carry the mixed solution of infusion fluid from the infusion fluid preparation assembly 108 to the blood circuit 17 for infusion into the patient. Alternatively, the infusion line 109 may also be directly connected to a vascular access of the patient. An intercepting element 109a, namely an infusion valve 109a, is provided on the infusion line 109 and configured to allow or prevent passage of the mixed solution of infusion fluid towards the blood circuit 17. An additional infusion fluid pump 111 may also be provided on the infusion line 109 downstream to the filter 107 (if necessary): in particular the infusion fluid pump 111 may be a volumetric pump (if inside the machine body) or an occlusive pump, such as a peristaltic pump, connected to the control unit 12, the latter being configured to control the fluid pump 111 to determine a desired flow rate of the infusion fluid towards the patient. Note that FIG. 4 provides for two separate pumps, namely pump 111 and pump 43, for infusing fluid into the extracorporeal blood circuit. It is clear that infusion line 109 may be alternatively directly connected to infusion line 39 (e.g., upstream) pump 43. If the infusion line is connected upstream ultrafilter 44, e.g. at branch 46, then the two ultrafilters 107a and 107b of FIGS. 2 and 3 may be coincident with ultrafilters 107 and 44. Further, infusion line 109 is shown to directly infuse the infusion fluid in post-infusion and in particular directly into the air separator 19.

Of course post infusion may occur in any other position in the blood return line, or, in case, also in the blood withdrawal line 6, for example in a location between the blood pump 21 and the filtration unit 2. The fluid circuit 32 may further comprise a bridging line 110 interposed in fluid connection between the infusion line 109 and the supply line 108. In particular the bridging line 110 is connected to the supply line 8 at a branch point 112 located downstream to the concentrated sources 27, 28 of the dialysis fluid preparation assembly 9 and, optionally, upstream to the conductivity sensor 35 and the flow meter 41 (FIG. 4). Alternatively, the bridging line 110 may be connected to the first preparation line 9a at a branch point located upstream to the concentrated sources 27, 28 of the dialysis fluid preparation assembly 9. This configuration is represented in FIG. 2. An intercepting element 110a, namely a bridging valve 110a, may also be arranged on the bridging line 110 to allow or prevent fluid passage between the infusion line 109 and the supply line 108. When the mixed solution of infusion fluid is delivered into the supply line 8, the infusion fluid and the dialysis fluid are mixed up defining an auxiliary mixed solution of dialysis fluid directed to the inlet of the secondary chamber 4 of the filtration unit 2. The fluid circuit 32 also comprises sensor 35 arranged on the supply line 8 or on the first preparation line 9a downstream with respect to the concentrated sources 27, 28 of the dialysis fluid preparation assembly 9. The control unit 12 is connected to the conductivity sensor 35 and is configured to receive and elaborate said conductivity signal: in particular when the infusion fluid preparation assembly injects the infusion fluid upstream (FIG. 2) or downstream (FIG. 4) of the dialysis fluid preparation assembly, sensor 35 monitors the conductivity or concentration of the auxiliary mixed solution of dialysis fluid before reaching the filtration unit 2. The fluid line 32 may also comprise the flow meter 41 arranged on the supply line 8 downstream to the dialysis fluid preparation assembly 9 (an additional flowmeter 105 is provided in the first preparation line 9a): in particular the flow meter 41 is arranged downstream with respect to the concentrated sources 27, 28 of the dialysis fluid preparation assembly 9 and is configured to provide a signal representative of a flow rate of the mixed solution of dialysis fluid. Alternatively, the flow meter 41 is configured to provide a signal representative of a flow rate of both the mixed solution of dialysis fluid and the auxiliary mixed solution of dialysis fluid when the on-line prepared infusion fluid is routed to the supply line 8 through the bridging line 110. The control unit 12 is connected to the flow meter 41 and is configured to receive and elaborate said flow rate signal.

The fluid circuit 32 also comprises a dialysis fluid pump 25, connected to the control unit 12, arranged on the supply line 8 and configured to determine a flow rate of the dialysis fluid. The control unit 12 is configured to control the start, stop and speed of the fluid pump 25 so that a desired dialysis flow rate is determined.

The fluid circuit 32 may also comprise a further semipermeable membrane filter, not shown in the attached figures, arranged on the supply line 8 between the dialysis fluid preparation assembly 9 and the filtration unit 2, in particular downstream of the dialysis pump 25.

The supply line 8 may branch, at branch point 46, into the auxiliary infusion line 39, which, in the example of FIG. 4, is shown directly connected to the blood return line 7, in particular to the air separator 19 (solid line) via post infusion tract 47b. Alternatively, the infusion line 39 may infuse infusion fluid in the blood withdrawal line 6 via pre-infusion tract 47a, in particular downstream the blood pump 21

(dotted line) at pre-infusion branch point 48. An embodiment includes an infusion line 39 branching into a pre-infusion branch 47a and in a post infusion branch 47b directing infusion fluid, respectively, in the blood withdrawal line 6 and in the blood return line 7. One or more infusion pumps 43 may be used to pump the desired flow of infusion fluid into the blood circuit. The infusion pump 43 may be a positive displacement pump (e.g. a peristaltic pump as shown) or any other pump configured to displace infusion fluid (e.g. a volumetric pump).

The dialysis effluent line 13 may be provided with a dialysate pump 26 and a flow meter 42. The flow meters 41, 42 respectively of the dialysis supply line 8 and of the dialysis effluent line 13 (plus—if necessary—the flow meter 105 on the auxiliary preparation line) may be used to control the fluid balance of a patient connected to the blood circuit 17 during a dialysis session. A sensor 11 is also provided on the dialysis effluent line 13, immediately downstream the filtration unit 2, to measure a parameter value of the dialysate in the dialysate effluent line 13. In more detail, the parameter of the dialysate, which is measured by the sensor 11 is conductivity of the dialysate or concentration of at least a substance in the dialysate. In detail the sensor 11 is a conductivity sensor, which is connected to the dialysis effluent line 13, and is configured to detect conductivity values of the dialysate downstream of the filtration unit 2. Alternatively (or in combination) sensor 11 may include a concentration sensor configured for measuring the concentration of at least one substance in the dialysate, such as sodium concentration. In addition, the apparatus may also include a disinfectant source 33, i.e. a disinfectant liquid solution, connected through a delivery line 38 to e.g., the first preparation line 9a or to the inlet duct 14a. An intercepting element 31, i.e. a clamp or a hydraulic valve connected to and commanded by the control unit 12, may also be arranged on the delivery line 38 of the disinfectant source 33.

An intercepting element 34, namely an inlet valve 34, may be provided on the first preparation line 9a and interposed between the water inlet duct 14a and the concentrated sources 27, 28 of the dialysis preparation assembly 9. In particular the inlet valve 34 is arranged upstream of any of the concentrated sources 27, 28 of the dialysis fluid preparation assembly 9. In other terms, the inlet valve 34, commanded by the control unit 12, allows or prevent passage of water from the inlet duct 14a to the dialysis fluid preparation assembly 9.

The control unit 12 of the dialysis apparatus represented in FIG. 4 is connected to the (graphic) user interface 22 through which it may receive instructions, for example a patient prescription including target values, such as blood flow rate, dialysis fluid flow rate, infusion fluid flow rate (pre infusion and/or post infusion), patient weight loss WL. The control unit 12 further receives the desired treatment, among those deliverable by the apparatus, such as ultrafiltration, hemodialysis, hemofiltration, hemodiafiltration, or specific treatments such as AFB or AFBK treatment as below briefly discussed. The control unit 12 furthermore may receive detected values by the sensors of the apparatus, such as the aforementioned flow meters 41, 42, the (e.g. conductivity) sensor 35 of the dialysis fluid preparation assembly 9 and the (e.g. conductivity) sensor 11 in the dialysis effluent line 13. The control unit 12 is further configured to control one or more of the intercepting elements of the apparatus 1 between the closed and open positions to determine a fluid flow configuration defined in terms of fluid paths: indeed, open or close positions of the intercepting elements determine one or more fluid flow configurations as shown for example in FIGS. 2 and 3. FIGS. 2 and 3 show a simplified scheme of the hydraulic circuit 200 in order to highlight in a more clear and immediate way the fluid paths within the hydraulic circuit according to different operation modes.

Figure 5:
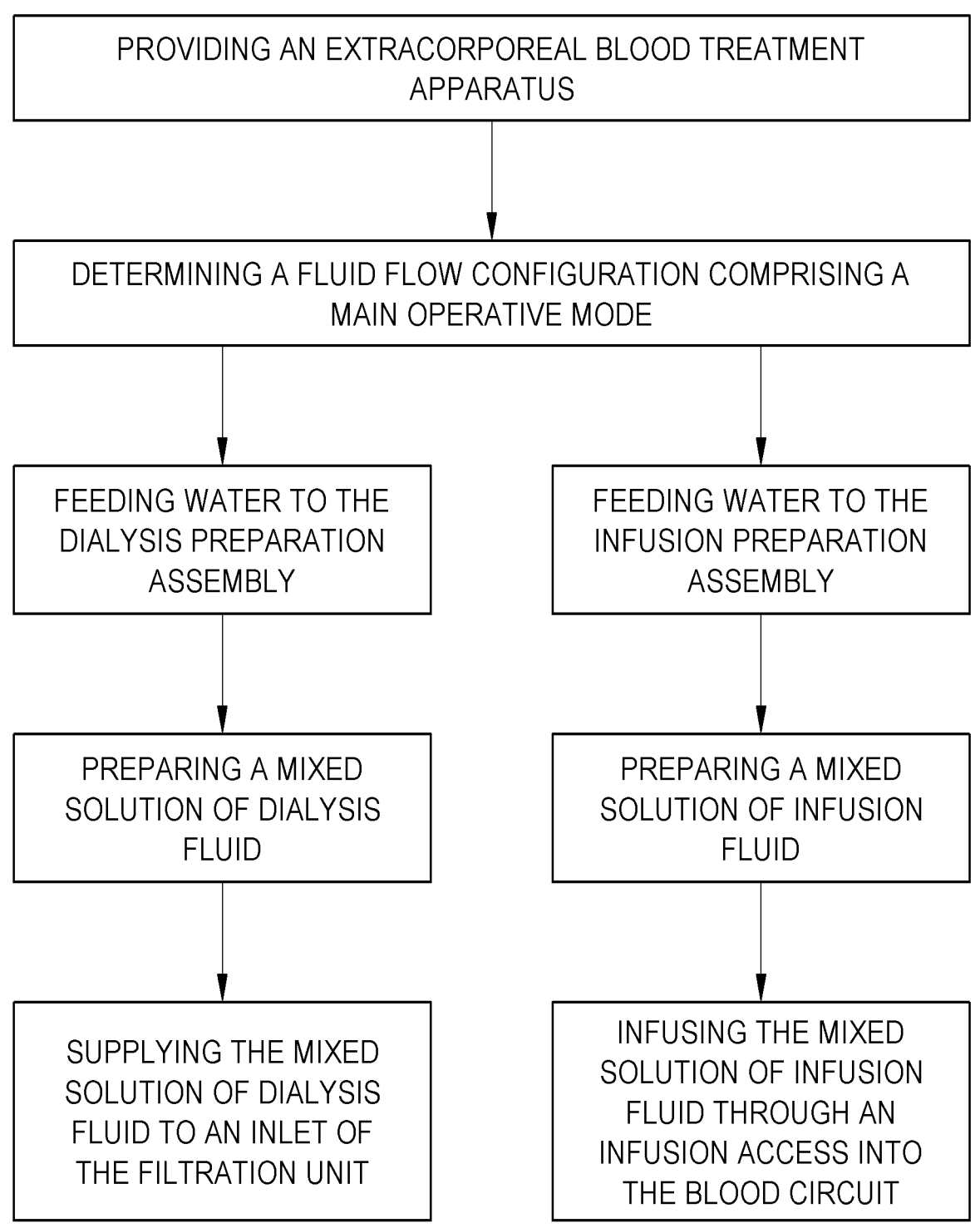
FIG. 5 is a block diagram illustrating the method for blood treatment herein described.

From the operative point of view, the fluid flow configuration comprises a main operative mode, schematically shown in FIG. 3, wherein the mixed solution of dialysis fluid is suppliable to an inlet of the secondary chamber 4 of the filtration unit 2, and the mixed solution of infusion fluid is infusible through the access point 19 into the blood circuit 17. FIG. 5 shows a flow chart of the steps carried out by the control unit to deliver fluid in the main operative mode once the apparatus is provided (block 201) and the control unit has configured the hydraulic circuit in the configuration configured to deliver two distinct fluids, namely the dialysis fluid and the infusion fluid (block 202). In detail, in the main operative mode, water is allowed to reach the dialysis preparation assembly 9 (namely the control unit 12 opens the corresponding valve letting water reach the mixing points where the concentrate lines inject concentrate into water (block 203). In the dialysis preparation assembly 9 the dialysis fluid is prepared by properly mixing water and concentrates and by controlling (at least) the conductivity of the prepared dialysis fluid (block 204); the outlet of the dialysis preparation assembly 9 is fluidly connected to the inlet of the secondary chamber 4 of the filtration unit 2 to supply dialysis fluid to the filtration unit for exchange with blood (block 205). Substantially simultaneously, in the same main operative mode, water is allowed to reach the infusion preparation assembly 108 (block 206). Here, water is mixed with the concentrate/s of the infusion preparation assembly 108 to prepare the infusion fluid (block 207), and the outlet of the infusion preparation assembly 108 is fluidly connected to the access point 19 of the blood circuit 17 to infuse into blood (block 208). According to the same main operative mode, the mixed solution of dialysis fluid may be supplied to the inlet of the secondary chamber 4 of the filtration unit 2 simultaneously to the infusion of the mixed solution of infusion fluid into the blood circuit 17. In a non-represented alternative requiring some minor flow path changes to the schematic of FIG. 3, but still according to the same main operative mode, the mixed solution of dialysis fluid may be supplied continuously into the blood circuit 17 while the mixed solution of infusion fluid may be supplied to the inlet of the secondary chamber 4 of the filtration unit 2.

According to what above, the apparatus is configured to perform an on-line preparation of both the mixed solution of dialysis fluid, to be provided to the filtration unit 2, and the mixed solution of infusion fluid to be infused into the blood circuit, in particular a mixed bicarbonate solution. Notably, in the main operative mode the mixed solution of infusion fluid is not mixed up with the mixed solution of dialysis fluid within the fluid circuit 32: therefore, in the main operation mode, a conductivity value of the mixed solution of dialysis fluid does not directly affect a conductivity value of the mixed solution of infusion fluid; the two treatment fluids are kept separate and separately routed to the filtration unit and to the blood circuit.

According to an embodiment, the main operation mode implies that the inlet valves 34, 100a of the first and second preparation lines 9a, 108a are in the open position, the bridging valve 110a is in the closed position, the dialysis fluid pump 25 determines dialysis fluid flow towards the secondary chamber 4 of the filtration unit 2, and the infusion fluid pump 106, 111 of the infusion line 109 determines infusion fluid flow towards the access point 19 of the blood circuit 17 or directly in a vascular access of the patient.

The fluid flow configuration further comprises a second operative mode, shown in FIG. 2, wherein the mixed solution of infusion fluid and the mixed solution of dialysis fluid are mixed up defining the auxiliary mixed solution of dialysis fluid flowing in the supply line 8. In the second operative mode the auxiliary mixed solution of dialysis fluid is suppliable to the inlet of the secondary chamber 4 of the filtration unit 2 to allow blood treatment and/or to the blood circuit through line 109 at infusion point 19. Notably, in the second operative mode the dialysis preparation assembly 9 is fluidly connected in series, upstream or downstream, with respect to the infusion preparation assembly 108: in other terms, in the second operative mode the first preparation line 9a is fluidly connected in series, upstream or downstream, with respect to the second preparation line 108a. According to an embodiment, in the second operative mode, the dialysis preparation assembly 9 is fluidly connected downstream to the infusion preparation assembly 108. The expression "fluidly connected in series" refers to the path of the fluid flow within the circuit determined by the open or closed state of the intercepting elements: therefore said expression does not refer to a physical arrangement of the first and the second preparation lines, which are still arranged as two branches connected to the same inlet duct 14a.

Notably, in the second operative mode, the auxiliary mixed solution of dialysis fluid is prepared based on substances infused in the water stream by the dialysis preparation assembly 9 and by the infusion preparation assembly 108, which are fluidly connected in series. Therefore, de facto, the auxiliary mixed solution of dialysis fluid is obtained by subsequent infusions of different substances provided by both the dialysis preparation assembly 9 and the infusion preparation assembly 108.

The fact that in the claims and description it is referred to the auxiliary mixed solution of dialysis fluid as obtained by mixing up the "mixed solution of dialysis fluid" and "mixed solution of infusion fluid" is due for sake of wording consistency: indeed the, as the dialysis preparation assembly 9 and the infusion preparation assembly 108 are fluidly connected in series, there is no anymore a sharp distinction between the "mixed solution of dialysis fluid" and the "mixed solution of infusion fluid", while on the contrary the auxiliary mixed solution of dialysis fluid derives from a continuous addition of substances.

Further, in the second operative mode, the intercepting elements may be commanded so that the auxiliary mixed solution of dialysis fluid is also (or exclusively) infused into the blood circuit 17. The fluid flow configuration further may also comprise a third operative mode (using the hydraulic circuit of FIG. 4) wherein the mixed solution of infusion fluid and the mixed solution of dialysis fluid are mixed up defining an auxiliary mixed solution of dialysis fluid flowing in the supply line 8 (analogously to what happens in the second operation mode): the auxiliary mixed solution of dialysis fluid is suppliable to the inlet of the secondary chamber 4 of the filtration unit 2. Anyhow, differently to the second operation mode, in the third operative mode the dialysis preparation assembly 9 is fluidly connected in parallel with respect to the infusion preparation assembly 108: in particular in the third operative mode the first preparation line 9a is fluidly connected in parallel with respect to the second preparation line 108a, wherein the outlet of the first preparation line 9a converges together with the outlet of the second preparation line 108a into the supply line 108. Further, in the third operative mode, the intercepting elements may be commanded so that the auxiliary mixed solution of dialysis fluid is also infused into the blood circuit 17. The graphical user interface 22, operatively connected to the control unit 12, is configured to receive, from a user, one or more inputs to select at least one of the fluid flow configurations, namely the main operation mode or the second operation mode or third operation mode. In a further detail, the main and the second operating mode may be used to provide different treatments with different dialysis solutions within the same dialysis apparatus. In particular, the main operating mode (FIG. 3) may be used to deliver on-line Acetate Free Bio-filtration (AFB) or Acetate Free Bio-filtration with Potassium profile (AFBK). In this respect, concentrate solution 103 is a buffer concentrate, in particular a sodium bicarbonate concentrate (e.g, dry powder concentrate such as Bicart® from Baxter) to on-line prepare a continuous bicarbonate solution to be infused into the extracorporeal blood treatment. The buffer (e.g., bicarbonate) solution is used in combination with a dialysis fluid with (substantially) no buffer, in particular with no bicarbonate content.

The acid-base balance in the patient is regulated by properly regulating the sodium bicarbonate solution infusion prepared by the infusion fluid preparation assembly 108.

At the same time, the dialysis fluid preparation assembly 9 prepares a dialysis fluid including the main electrolytes. One or two concentrate containers or bags 27, 28 may be used. In a first example, AFB treatment is delivered, wherein the electrolyte content in the dialysis fluid is determined by the prescription and maintained substantially constant in its relative electrolyte content throughout the entire treatment.

In a second example, AFBK treatment, two concentrate containers 27, 28 are used. The two concentrates have different potassium concentration and an identical concentration of the other electrolytes. Therefore, by variating the infusion ratio between the two concentrate containers, the potassium may be properly profiled during the treatment. For example, the content of the two concentrate bags 27, 28 may include the following substances in the concentration ranges after proper dilution as indicated:

| Concentrate 1 | Concentrate 2 | Concentration after dilution | |
|---|---|---|---|
| $Na^{++}$ | $Na^{++}$ | 130-160 (140)* | mmol/l |
| $K^+$ | | 6.5-9 (7.5) | mmol/l |
| | $K^+$ | 0-3 (0)* | mmol/l |
| $Ca^{++}$ | $Ca^{++}$ | 1-3 (2)* | mmol/l |
| $Mg^{++}$ | $Mg^{++}$ | 0.2-0.6 (0.4)* | mmol/l |
| $Cl^-$ | $Cl^-$ | 130-170 (140-160)* | mmol/l |
| $Glucose/C_6H_{12}O_6$ | $Glucose/C_6H_{12}O_6$ | 0-10 (5.5)* | mmol/l |

*narrower concentrations are indicated between brackets

According to this embodiment, the concentrated source 28 of the dialysis fluid preparation assembly 9 comprises no potassium, wherein the concentrate pump 30 is operative on the delivery line 37 interposed between the concentrated source 28 and the first preparation line 9a to deliver a predefined flow rate of the concentrated solution of the other electrolytes into the first preparation line 9a. Differently, the concentrated source 27 contains a slightly high concentration of potassium and concentrations for the other ions similar/identical to the concentration for the same other ions in the concentrated source 28. The control unit 12 is further configured to command the dialysis preparation assembly 9 to obtain a predetermined potassium concentration value into the mixed solution of the dialysis fluid, wherein the potassium concentration value may be assumed based on the control of the concentrate pumps 29 and 30 to deliver the differently concentrated solution of potassium. The desired potassium concentration value may be set constant during the blood treatment session: alternatively, the desired potassium concentration value may be variable during the blood treatment session according to a predefined potassium profiling curve.

In more detail, the potassium profiling curve may imply a decreasing potassium concentration over time, for example according to the following formula:

$$K(t) = K_{INI} + (K_F - K_{INI}) \cdot \left( \frac{t - T_{delay}}{T_{dialysis} - T_{delay}} \right)^{0.5}$$

$$\text{where } T_{delay} < t < T_{dialysis}$$

wherein:

K(t) is an actual value of potassium concentration in the mixed solution of dialysis fluid;

$K_{ini}$ is an initial value of potassium concentration in the mixed solution of dialysis fluid;

$K_F$ is a final value of potassium concentration in the mixed solution of dialysis fluid;

$T_{delay}$ is an initial time delay of the potassium delivery start;

$T_{dialysis}$ is the length of the blood treatment;

t is the current treatment time.

At the beginning of the blood treatment session up to a t=$T_{delay}$, the potassium concentration value is set constant and equal to $K_{ini}$.

The concentrated sources 27, 28 may be disposable plastic containers or bags housing the respective concentrate substance in liquid form: according to the embodiment wherein the potassium profiling curve is provided, the dialysis fluid preparation assembly 9 may comprise Safebag® KV93G and Safebag® KV95G from Baxter.

In case only one formulation for the dialysis fluid and for any possible infusion fluid is required, then the second operative condition is advantageously used. This is the case of usual HD, HF and HDF chronic treatments. In this configuration, represented in FIG. 2, the concentrate container 103 still contain the buffer, for example sodium bicarbonate (optionally in powder/dry form). In this case, Bicart® cartridge from Baxter may be used again. A second concentrate A is then used containing the electrolytes, for example SelectBag® or SelectBag Citrate® from Baxter may be used. In this embodiment, the purified water is firstly mixed with sodium bicarbonate and the buffer containing fluid is then mixed with the electrolytes contained in first and/or second bag 27, 28 to produce a proper dialysis fluid. Given the hydraulic circuit schematically shown in FIGS. 2 and 3, the same configuration will be therefore properly configured and suitable to deliver standard dialysis on-line treatment and to deliver AFB and AFBK on-line treatment. As already mentioned, the described embodiments are intended to be non-limiting examples. In particular the circuits of FIG. 1 should not be interpreted as defining or limiting, as an apparatus such as in the invention may comprise other additional or alternative components to those described. For example an ultrafiltration line may be included, with at least one respective pump connected to the dialysis effluent line 13. The blood circuit of FIG. 4 is intended for double needle treatments: however, this is a non-limiting example of the blood set. Indeed, the apparatus may be configured to perform single needle treatments, i.e.

the patient is connected to the extracorporeal blood circuit by way of a single needle and the extracorporeal line from the patient is then split into a withdrawal line and a return line, using, for example, a 'Y' connector. During single needle treatment, a blood withdrawal phase removing blood from patient is alternated to a blood return phase in which blood is restituted to the patient. Furthermore one or more devices for measuring substance concentrations might be implemented either (or both) in the dialysis fluid side or (and) in the blood side of the hydraulic circuit. Concentration of calcium, potassium, magnesium, bicarbonate, and/or sodium might be desired to be known. Finally, the above-cited one or more pumps and all the other temperature, pressure, and concentration sensors may operate either on the dialysis fluid supply line 8 and/or on the dialysis effluent line 13, in order to adequately monitor the preparation and movement of the liquid in the hydraulic circuit.

The invention claimed is:

1. An apparatus for extracorporeal blood treatment comprising:

a filtration unit having a primary chamber and a secondary chamber separated by a semi-permeable membrane;

a blood circuit comprising:

a blood withdrawal line extending between a first end connected to an inlet of the primary chamber and a second end for connection to a patient, and a blood return line extending between a first end connected to an outlet of the primary chamber and a second end for connection to said patient;

a fluid circuit comprising:

one or more water inlet ducts for receiving water, a dialysis preparation assembly comprising one or more concentrated sources housing a respective concentrate solution and configured to prepare a mixed solution of dialysis fluid, at least one of said one or more water inlet ducts to provide water to the dialysis preparation assembly for preparing said mixed solution of dialysis fluid, and an infusion preparation assembly, separate and distinct from the dialysis preparation assembly, comprising one or more concentrated sources housing a respective concentrate solution and configured to prepare a mixed solution of infusion fluid, at least one of said one or more water inlet ducts configured to provide water to the infusion preparation assembly for preparing said mixed solution of infusion fluid;

intercepting elements arranged and operative at least along the fluid circuit and configured to move between a closed position, wherein a fluid passage is interdicted, and an open position wherein fluid passage is allowed; and a control unit configured to control one or more of said intercepting elements between the closed position and the open position to determine a fluid flow configuration defining different fluid paths, said fluid flow configuration comprising a main operative mode wherein:

at least one of said one or more water inlet ducts is configured to provide water to the dialysis preparation assembly for preparing said mixed solution of dialysis fluid, wherein the mixed solution of dialysis fluid is suppliable to an inlet of the secondary chamber of the filtration unit, and at least one of said one or more water inlet ducts is configured to provide water to the infusion preparation assembly for preparing said mixed solution of infusion fluid, wherein the mixed solution of infusion fluid is infusible through an infusion access point into the blood circuit, wherein said fluid flow configuration comprises at least a second operative mode in which the dialysis preparation assembly and the infusion preparation assembly cooperate to prepare an auxiliary mixed solution of dialysis fluid different from the mixed solution of dialysis fluid and from the mixed solution of infusion fluid.

2. The apparatus of claim 1, further comprising:

a supply line extending between an outlet of the dialysis preparation assembly and the inlet of the secondary chamber of the filtration unit, and an infusion line extending between an outlet of the infusion preparation assembly and the infusion access point of the blood circuit, wherein in the main operative mode:

the outlet of the dialysis preparation assembly is fluidly connected to the inlet of the secondary chamber of the filtration unit, the outlet of the infusion preparation assembly is fluidly connected to the blood circuit, and the one or more water inlet ducts being configured to supply water independently and, through different tube segments, directly to both the dialysis preparation assembly and the infusion preparation assembly;

wherein the control unit is configured to control the dialysis preparation assembly and the infusion preparation assembly to respectively prepare the mixed solution of dialysis fluid and the mixed solution of infusion fluid so that the mixed solution of dialysis fluid is different in composition from the mixed solution of infusion fluid, the dialysis fluid being different from the infusion fluid due to:

a nature of one or more solutes; and/or a concentration of one or more solutes; and wherein the mixed solution of dialysis fluid is supplied to the inlet of the secondary chamber of the filtration unit simultaneously with an infusion of the mixed solution of infusion fluid into the blood circuit.

3. The apparatus of claim 2, wherein the infusion line extends between the outlet of the infusion preparation assembly and the infusion access point placed at the blood return line of the blood circuit, the outlet of the infusion preparation assembly being fluidly connected to the blood return line of the blood circuit.

4. The apparatus of claim 1, wherein in the second operative mode:

the mixed solution of infusion fluid and the mixed solution of dialysis fluid are mixed so as to define the auxiliary mixed solution of dialysis fluid flowing in a supply line, wherein the auxiliary mixed solution of dialysis fluid is suppliable to the inlet of the secondary chamber of the filtration unit and/or is infusible into the blood circuit, and wherein, in said second operative mode, the dialysis preparation assembly is fluidly connected in series, upstream or downstream, with respect to the infusion preparation assembly, and a first preparation line is fluidly connected in series with respect to a second preparation line.

5. The apparatus of claim 1, wherein in the main operative mode, one of concentrated sources of the dialysis preparation assembly comprises concentrated electrolytes, including sodium, calcium and potassium, and another one of the concentrated sources of the dialysis preparation assembly comprises concentrated electrolytes, including sodium and calcium.

6. The apparatus of claim 5, wherein a potassium concentration in the one of the concentrated sources is different from the potassium concentration in another one of the concentrated sources; and wherein concentrations of other electrolytes different from potassium are equal in the concentrated sources and in the another one of the one or more concentrated sources.

7. The apparatus of claim 1, wherein at least one concentrated solution housed into the one or more concentrated sources of the infusion preparation assembly comprises a buffer substance from the group including bicarbonate, citrate, lactate and acetate; and wherein in the main operative mode, the at least one concentrated solution housed into the one or more concentrated sources of the infusion preparation assembly comprises bicarbonate.

8. The apparatus of claim 4, comprising:

a first conductivity sensor arranged in the dialysis preparation assembly along the first preparation line downstream with respect to the one or more concentrated sources, the first conductivity sensor configured to provide a first signal representative of an electrical conductivity of the mixed solution of dialysis fluid, and of an electrical conductivity of the auxiliary mixed solution of dialysis fluid, wherein the control unit is configured to receive the first signal representative of the electrical conductivity to determine an actual conductivity and to compare the actual conductivity to a target conductivity, the control unit driving the dialysis preparation assembly to reduce a difference between the actual conductivity and the target conductivity; and a second conductivity sensor arranged in the infusion preparation assembly along the second preparation line downstream with respect to the one or more concentrated sources of the infusion preparation assembly, the second conductivity sensor configured to provide a second signal representative of an electrical conductivity of the mixed solution of infusion fluid, wherein the control unit is configured to receive the second signal representative of the electrical conductivity to determine the actual conductivity and to compare the actual conductivity to a target conductivity, the control unit driving the infusion preparation assembly to reduce the difference between the actual conductivity and the target conductivity.

9. The apparatus of claim 1, wherein the fluid circuit comprises a bridging line interposed in fluid communication between an infusion line and a supply line, wherein the intercepting elements comprise one or more of:

a bridging valve arranged along the bridging line to allow or interdict fluid flow between the infusion line and the supply line;

an infusion valve arranged along the infusion line to allow or prevent the infusion fluid to flow towards the infusion access point; and a first inlet valve arranged along a first preparation line, said first inlet valve being interposed between the one or more water inlet duct and the one or more concentrated sources of the dialysis preparation assembly; or a second inlet valve arranged along a second preparation line, said second inlet valve being interposed between the water inlet duct and the one or more concentrated sources of the infusion preparation assembly.

10. The apparatus of claim 9, wherein in a main operation mode:

the first and second inlet valves of the first and second preparation lines are in the open position;

the bridging valve is in the closed position;

a dialysis fluid pump determines dialysis fluid flow towards the secondary chamber of the filtration unit; and an infusion pump of the infusion line determines infusion fluid flow towards the infusion access point of the blood circuit or directly in a vascular access of the patient;

and wherein in a second operation mode:

the inlet valve of the first preparation line is in the closed position;

the inlet valve of the second preparation line is in the open position;

the bridging valve is in the open position;

the dialysis fluid pump determines the dialysis fluid flow towards the secondary chamber of the filtration unit; and and the infusion pump of the infusion line is not active.

11. The apparatus of claim 1, wherein the fluid circuit includes:

a water inlet duct for receiving water, said water inlet duct branching into a water line to feed water directly to the infusion preparation assembly and into a water branch to feed water directly to the dialysis preparation assembly, wherein the intercepting elements comprise one or more valves to allow or prevent water from flowing in the water line and/or in the water branch;

a bridging line fluidly connecting an outlet of the infusion preparation assembly with an inlet to the dialysis preparation assembly, wherein the intercepting elements comprise one or more valves to allow or prevent water from flowing in the bridging line;

an infusion line connected to an outlet of the infusion preparation assembly routing the infusion fluid to the blood circuit, the infusion line including an on-line port and a tube portion connecting the outlet of the infusion preparation assembly to the on-line port, wherein the tube portion connecting the outlet of the infusion preparation assembly to the on-line port includes an infusion pump;

a supply line connected to an outlet of the dialysis preparation assembly routing the infusion fluid to the filtration unit; and a connecting line fluidly connecting the infusion line and the supply line, wherein the intercepting elements comprise one or more valves to allow or prevent fluid from flowing into the connecting line.

12. The apparatus of claim 11, wherein in the main operation mode, the control unit is configured to drive:

the one or more valves to allow water flow towards both (i) the dialysis preparation assembly through the water branch and (ii) the infusion preparation assembly through the water line;

the one or more valves to prevent fluid flow through the bridging line between the outlet of the infusion preparation assembly and the inlet of the dialysis fluid preparation assembly; and the one or more valves in the connecting line to prevent fluid flow through the connecting line between the infusion line and the supply line.

13. The apparatus of claim 11, wherein the tube portion connecting the outlet of the infusion preparation assembly to the on-line port includes at least one infusion ultrafilter placed between a connecting line fluidly connecting the tube portion with an outlet of the dialysis preparation assembly and the on-line port, and/or wherein the on-line port is an access placed on an external portion of a cabinet of the apparatus, the on-line port being configured for a connection of a disposable tubing directing fluid to the blood circuit.

14. The apparatus of claim 1, wherein the fluid circuit comprises a joining tubing fluidly connecting a supply line to an infusion line downstream of an infusion pump placed on the infusion line and connecting the supply line downstream of an infusion ultrafilter, the intercepting elements comprising one or more valves to allow or prevent fluid from flowing in the joining tubing, wherein in a main operation mode, the control unit drives the one or more valves to prevent fluid flow through the joining tubing between the infusion line and the supply line, and wherein the joining tubing connects the supply line to an on-line port of the infusion line.

15. The apparatus of claim 1, wherein the fluid circuit includes a water inlet duct for receiving water, said water inlet duct branching into a water line to feed water directly to the infusion preparation assembly and into a water branch to feed water directly to the dialysis preparation assembly, wherein the fluid circuit comprises an inlet flow meter placed on the water inlet duct upstream the branching and an effluent line flow meter on an effluent line, and wherein at least in a main operation mode, the control unit is configured to:

receive or calculate a set ultrafiltration rate to be achieved during the extracorporeal blood treatment; and drive the apparatus to achieve the set ultrafiltration rate based on a difference between an effluent flow rate, measured with the effluent line flow meter, and a sum of an infusion flow rate and a dialysis flow rate, measured with the inlet flow meter.

16. The apparatus of claim 1, wherein the fluid circuit comprises a supply line flow meter on the supply line, an infusion line flow meter on the infusion line and an effluent line flow meter on an effluent line, wherein, in a main operating mode, the control unit receive signals from the supply line flow meter, the infusion line flow meter and the effluent line flow meter to control an ultrafiltration rate through the filtration unit, wherein the control unit receives or calculates a set ultrafiltration rate to be achieved during the extracorporeal blood treatment and drives the apparatus to achieve the set ultrafiltration rate based on the signals received from the supply line flow meter, the infusion line flow meter and the effluent line flow meter based on a difference between an effluent flow rate and the sum of the infusion flow rate, measured with the infusion line flow meter, and a dialysis flow rate.

17. The apparatus of claim 2, wherein the control unit is configured to control the one or more of the intercepting elements between the open position and the closed position to allow or prevent the infusion line to be in fluid communication with the supply line.

18. The apparatus of claim 2, wherein the fluid circuit defines a fluid line net comprising the dialysis preparation assembly, the infusion preparation assembly, the infusion line, the supply line and the intercepting elements, and wherein the dialysis preparation assembly, the infusion preparation assembly, the infusion line, and the supply line are in fluid communication with each other through said fluid line net and fluidly connectable with each other based on the open position or the closed position of the intercepting elements.

19. The apparatus of claim 1, wherein the control unit is configured to control the one or more of said intercepting elements between the open position and the closed position to allow or prevent the dialysis preparation assembly to be in fluid communication with the infusion preparation assembly, and to allow or prevent the mixed solution of dialysis fluid prepared in the dialysis preparation assembly to be in fluid communication with the infusion preparation assembly, or the mixed solution of infusion fluid prepared in the infusion preparation assembly to be in fluid communication with the dialysis preparation assembly.

20. The apparatus of claim 1, wherein the dialysis preparation assembly and the infusion preparation assembly are in fluid communication with each other through fluid lines defining a fluid line net comprising the intercepting elements, the control unit being configured to control the one or more of said intercepting elements between the open position and the closed position to define two or more fluid paths for the mixed solution of dialysis fluid and for the mixed solution of infusion fluid.

21. The apparatus of claim 20, wherein said two or more fluid paths comprise at least one fluid path in which the mixed solution of dialysis fluid prepared by the dialysis preparation assembly is not mixed with the mixed solution of infusion fluid prepared by the infusion preparation assembly and another further fluid path, wherein either:

the fluid prepared by the dialysis preparation assembly enters into the infusion preparation assembly;

the fluid prepared by the infusion preparation assembly enters into the dialysis preparation assembly; or the fluid prepared by the dialysis preparation assembly is mixed with the fluid prepared by the infusion preparation assembly.

22. The apparatus of claim 1, wherein in the second operative mode, the control unit is configured to control the intercepting elements to mix the mixed solution of dialysis fluid with the mixed solution of infusion fluid defining the auxiliary mixed solution of dialysis fluid.

23. An apparatus for extracorporeal blood treatment comprising:

a filtration unit having a primary chamber and a secondary chamber separated by a semi-permeable membrane;

a blood circuit comprising at least:

a blood withdrawal line extending between a first end connected to an inlet of the primary chamber and a second end for connection to a patient; and a blood return line extending between a first end connected to an outlet of the primary chamber and a second end for connection to said patient;

a fluid circuit comprising at least:

one or more water inlet ducts for receiving water;

a dialysis preparation assembly comprising one or more concentrated sources housing a respective concentrate solution and configured to prepare a mixed solution of a dialysis fluid, at least one of said one or more water inlet ducts to provide water to the dialysis preparation assembly for preparing said mixed solution of dialysis fluid; and an infusion preparation assembly, separate and distinct from the dialysis preparation assembly, comprising one or more concentrated sources housing a respective concentrate solution and configured to prepare a mixed solution of an infusion fluid, at least one of said one or more water inlet ducts to provide water to the infusion preparation assembly for preparing said mixed solution of infusion fluid, intercepting elements arranged and operative at least on the fluid circuit and configured to move between a closed position, wherein a fluid passage is interdicted, and an open position wherein fluid passage is allowed;

a control unit configured to control one or more of said intercepting elements between the closed position and the open position to determine a fluid flow configuration defining different fluid paths, said fluid flow configuration comprising a main operative mode wherein:

at least one of said one or more water inlet ducts is configured to provide water to the dialysis preparation assembly for preparing said mixed solution of dialysis fluid and the mixed solution of dialysis fluid is suppliable to an inlet of the secondary chamber of the filtration unit, and at least one of said one or more water inlet ducts is configured to provide water to the infusion preparation assembly for preparing said mixed solution of infusion fluid and the mixed solution of infusion fluid is infusible through an infusion access point into the blood circuit, wherein said fluid flow configuration further comprises a second operative mode wherein:

the mixed solution of infusion fluid and the mixed solution of dialysis fluid are mixed to create an auxiliary mixed solution of dialysis fluid flowing in a supply line, and the auxiliary mixed solution of dialysis fluid is suppliable to the inlet of the secondary chamber of the filtration unit and/or is infusible into the blood circuit, and wherein in said second operative mode, the dialysis preparation assembly is fluidly connected in series, upstream or downstream, with respect to the infusion preparation assembly, and a first preparation line is fluidly connected in series with respect to a second preparation line.

24. An apparatus for extracorporeal blood treatment comprising:

a filtration unit having a primary chamber and a secondary chamber separated by a semi-permeable membrane;

a blood circuit comprising at least:

a blood withdrawal line extending between a first end connected to an inlet of the primary chamber and a second end for connection to a patient, and a blood return line extending between a first end connected to an outlet of the primary chamber and a second end for connection to said patient;

a fluid circuit comprising at least:

one or more water inlet ducts for receiving water, a dialysis preparation assembly comprising one or more concentrated sources housing a respective concentrate solution and configured to prepare a mixed solution of a dialysis fluid, at least one of said one or more water inlet ducts to provide water to the dialysis preparation assembly for preparing said mixed solution of dialysis fluid, and an infusion preparation assembly, separate and distinct from the dialysis preparation assembly, comprising one or more concentrated sources housing a respective concentrate solution and configured to prepare a mixed solution of an infusion fluid, at least one of said one or more water inlet ducts to provide water to the infusion preparation assembly for preparing said mixed solution of infusion fluid;

intercepting elements arranged and operative at least on the fluid circuit and configured to move between a closed position, wherein a fluid passage is interdicted, and an open position wherein fluid passage is allowed; and a control unit configured to control one or more of said intercepting elements between the closed and open position to determine a fluid flow configuration defining different fluid paths, said fluid flow configuration comprising a main operative mode wherein:

at least one of said one or more water inlet ducts is configured to provide water to the dialysis preparation assembly for preparing said mixed solution of dialysis fluid and the mixed solution of dialysis fluid is suppliable to an inlet of the secondary chamber of the filtration unit, and at least one of said one or more water inlet ducts is configured to provide water to the infusion preparation assembly for preparing said mixed solution of infusion fluid and the mixed solution of infusion fluid is infusible through an infusion access point into the blood circuit, wherein said one or more water inlet ducts branches into a water line to feed water directly to the infusion preparation assembly and into a water branch to feed water directly to the dialysis preparation assembly, wherein intercepting elements comprises one or more valves to allow or prevent water from flowing in the water line and/or in the water branch.

25. An apparatus for extracorporeal blood treatment comprising:

a filtration unit having a primary chamber and a secondary chamber separated by a semi-permeable membrane;

a blood circuit comprising at least:

a blood withdrawal line extending between a first end connected to an inlet of the primary chamber and a second end for connection to a patient, and a blood return line extending between a first end connected to an outlet of the primary chamber and a second end for connection to said patient;

a fluid circuit comprising at least:

one or more water inlet ducts for receiving water, a dialysis preparation assembly comprising one or more concentrated sources housing a respective concentrate solution and configured to prepare a mixed solution of a dialysis fluid, at least one of said one or more water inlet ducts to provide water to the dialysis preparation assembly for preparing said mixed solution of dialysis fluid, and an infusion preparation assembly, separate and distinct from the dialysis preparation assembly, comprising one or more concentrated sources housing a respective concentrate solution and configured to prepare a mixed solution of an infusion fluid, at least one of said one or more water inlet ducts to provide water to the infusion preparation assembly for preparing said mixed solution of infusion fluid;

intercepting elements arranged and operative at least on the fluid circuit and configured to move between a closed position, wherein a fluid passage is interdicted, and an open position wherein fluid passage is allowed; and a control unit configured to control one or more of said intercepting elements between the closed position and the open position to determine a fluid flow configuration defining different fluid paths, said fluid flow configuration comprising a main operative mode wherein:

at least one of said one or more water inlet ducts is configured to provide water to the dialysis preparation assembly for preparing said mixed solution of dialysis fluid and the mixed solution of dialysis fluid is suppliable to an inlet of the secondary chamber of the filtration unit, and at least one of said one or more water inlet ducts is configured to provide water to the infusion preparation assembly for preparing said mixed solution of infusion fluid and the mixed solution of infusion fluid is infusible through an infusion access point into the blood circuit, wherein said fluid flow configuration comprises at least a second operative mode, and wherein the control unit is configured to control the intercepting elements to mix the mixed solution of dialysis fluid with the mixed solution of infusion fluid defining an auxiliary mixed solution of dialysis fluid.

* * * * *